US006576437B2

United States Patent
(12) United States Patent
Mercurio et al.

(10) Patent No.: US 6,576,437 B2
(45) Date of Patent: Jun. 10, 2003

(54) STIMULUS-INDUCIBLE PROTEIN KINASE COMPLEX AND METHODS OF USE THEREFOR

(75) Inventors: Frank Mercurio, San Diego, CA (US); Hengyi Zhu, San Diego, CA (US); Miguel Barbosa, San Diego, CA (US); Jian Wu Li, San Diego, CA (US); Brion W. Murray, San Diego, CA (US)

(73) Assignee: Signal Pharmaceuticals, Inc., San Diego, CA (US)

(*) Notice: Subject to any disclaimer, the term of this patent is extended or adjusted under 35 U.S.C. 154(b) by 0 days.

(21) Appl. No.: 09/844,908

(22) Filed: Apr. 27, 2001

(65) Prior Publication Data

US 2002/0151021 A1 Oct. 17, 2002

Related U.S. Application Data

(60) Division of application No. 08/910,820, filed on Aug. 13, 1997, now Pat. No. 6,258,579, which is a continuation-in-part of application No. 08/697,393, filed on Aug. 26, 1996, now Pat. No. 5,972,674.

(51) Int. Cl.[7] .......................... C12Q 1/48; C12P 21/02; C12N 9/12

(52) U.S. Cl. ......................... 435/15; 435/68.1; 435/194

(58) Field of Search .......................... 435/15, 68.1, 194

(56) References Cited

FOREIGN PATENT DOCUMENTS

WO WO 97/35014 9/1997

OTHER PUBLICATIONS

Barroga et al., "Constitutive phosphorylation of IkBx by casein kinase II," Proc. Natl. Acad. Sci. USA 92(17):7637–41, 1995.

Chen et al., "Site–Specific Phosphorylation of IkBx by a Novel Ubiquitination–Dependent Protein Kinase Activity," Cell 84:853–862, 1996.

Connelly and Marcu, "Chuk, A New Member of the Helix–Loop–Helix and Leucine Zipper Families of Interacting Proteins, Contains a Serine–Threonine Kinase Catalytic Domain," Cellular and Molecular Biology Research 41(6):537–549, 1995.

DiDonato et al., "Mapping of the Inducible IkB Phosphorylation Sites That Signal Its Ubiquitination and Degradation," Molecular and Cellular Biology 16(4):1295–1304, 1996.

Ghosh, S., "Activation in vitro of NF–kB by phosphorylation of its inhibitor IkB," Nature 344(6267):678–82, 1990.

Isreal A., "IkB kinase all zipped up," Nature 388:519–521, 1997.

Kumar et al., "Double–stranded RNA–dependent protein kinase activates transcription factor NF–kB by phosphorylation IkB," Proc Natl. Acad. Sci. USA 91(14):6288–92, 1994.

Kuno et al., "Identification of an IkBx–associated Protein Kinase in a Human Monocyctic Cell Line and Determination of Its Phosphorylation Sites on IkBx," The Journal of Biological Chemistry 270(46):27914–27919, 1995.

Maniatis, T., "Catalysis by a Multiprotein IkB Kinase Complex," Science 278:818–819, 1997.

Meco et al., "PKC induces phosphorylation and inactivation of IkB–x in vitro," EMBO Journal 13(12):2842–8, 1994.

Mercurio et al., "Biochemical Characterization and Purification of the IkB Kinase," The Faseb Journal 10(6):p. A1265, Abstract No. 1534, 1996.

Regnier et al., "Identification and Characterization of an IkB Kinase," Cell 90:373–383, 1997.

*Primary Examiner*—Charles L. Patterson, Jr.
(74) *Attorney, Agent, or Firm*—Mathews, Collins, Shepher & McKay, P.A.

(57) ABSTRACT

Compositions and methods are provided for treating NF-κB-related conditions. In particular, the invention provides a stimulus-inducible IKK signalsome, and components and variants thereof. An IKK signalsome or component thereof may be used, for example, to identify antibodies and other modulating agents that inhibit or activate signal transduction via the NF-κB cascade. IKK signalsome, components thereof and/or modulating agents may also be used for the treatment of diseases associated with NF-κB activation.

10 Claims, 28 Drawing Sheets

Interactions of IκBα Peptides with the Signalsome

```
                          10                  20                  30                  40                  50
IKK-1 M E R P P G L R P G A G G P W E M R E R L G T G G F G N V C L Y Q H R E L D L K I A I K S C R L E L
IKK-2 M S W S P S L T T Q T C G A W E M K E R L G T G G F G N V I R W H N Q E T G E Q I A I K Q C R Q E L

                          60                  70                  80                  90                 100
IKK-1 S T K N R E R W C H E I Q I M K K L N H A N V V K A C D V P E E L N - I L I H D V P L L A M E Y C S
IKK-2 S P R N R E R W C L E I Q I M R R L T H P N V V A A R D V P E G M Q N L A P N D L P L L A M E Y C Q

                         110                 120                 130                 140                 150
IKK-1 G G D L R K L L N K P E N C C G L K E S Q I L S L L S D I G S G I R Y L H E N K I I H R D L K P E N
IKK-2 G G D L R K Y L N Q F E N C C G L R E G A I L T L L S D I A S A L R Y L H E N R I I H R D L K P E N

                         160   A1            170                 180                 190                 200
IKK-1 I V L Q D V G G K I I H K I I D L G Y A K D V D Q G S L C T S F V G T L Q Y L A P E L F E N K P Y T
IKK-2 I V L Q Q G E Q R L I H K I I D L G Y A K E L D Q G S L C T S F V G T L Q Y L A P E L L E Q Q K Y T

                         210                 220                 230                 240                 250
IKK-1 A T V D Y W S F G T M V F E C I A G Y R P F L H H L Q P F T W H E K I K K K D P K C I F A C E E M S
IKK-2 V T V D Y W S F G T L A F E C I T G F R P F L P N W Q P V Q W H S K V R Q K S E V D I V V S E D L N

                         260                 270                 280                 290                 300
IKK-1 G E V R F S S H L P Q P N S L C S L I V E P M E N W L Q L M L N W D P Q Q R G G P V D L T L K Q P R
IKK-2 G T V K F S S S L P Y P N N L N S V L A E R L E K W L Q L M L M W H P R Q R G - - T D P T Y G P N G

                         310                 320                 330                 340                 350
IKK-1 C F V L M D H I L N L K I V H I L N M T S A K I I S F L L P P D E S L H S L Q S R I E R E T G I N T
IKK-2 C F K A L D D I L N L K L V H I L N M V T G T I H T Y P V T E D E S L Q S L K A R I Q Q D T G I P E

                         360                 370                 380                 390                 400
IKK-1 G S Q E L L S E T G I S L D P R K P A S Q C V L D G - - - - V R G C D S Y M V Y L F D K S K T V Y E
IKK-2 E D Q E L L Q E A G L A L I P D K P A T Q C I S D G K L N E G H T L D M D L V F L F D N S K I T Y E

                         410                 420                 430                 440                 450
IKK-1 G P F A S R S L S D C V N Y I V Q D S K I Q L P I I Q L R K V W A E A V H Y V S G L K E D Y S R L F
IKK-2 T Q I S P R P Q P E S V S C I L Q E P K R N L A F F H L R K V W G Q V W H S I Q T L K E D C N R L Q

                         460                 470                 480                 490      A3         500
IKK-1 Q G Q R A A M L S L L R Y N A N L T K M K N T L I S A S Q Q L K A K L E F F H K S I Q L D L E R Y S
IKK-2 Q G Q R A A M M N L L R N N S C L S K M K N S M A S M S Q Q L K A K L D F F K T S I Q I D L E K Y S

                         510                 520                 530                 540                 550
IKK-1 E Q M T Y G I S S E K M L K A W K E M E E K A I H Y A E V G V I G Y L E D Q I M S L H A E I M E L Q
IKK-2 E Q T E F G I T S D K L L L A W R E M E Q A V E L C G R E N E V K L L V E R M M A L Q T D I V D L Q

                         560                 570                 580                 590              B3 600
IKK-1 K S P Y G R R Q G D L M E S L E Q R A I D L Y K Q L K H R P S D - H S Y S D S T E M V K I I V H T V
IKK-2 R S P M G R K Q G G T L D D L E E Q A R E L Y R R L R E K P R D Q R T E G D S Q E M V R L L L Q A I

                         610   B2            620          B1    630   A2           640                 650
IKK-1 Q S Q D R V L K E R F G H L S K L L G C K Q K I I D L L P E V R V A L S N I K E A D N T V M F M Q G
IKK-2 Q S F E K K V R V I L T D L S K T V V C K Q K A L E L L P E V R E V V S L M N K D E K T V V R L Q E

                         660                 670                 680                 690                 700
IKK-1 K R Q K E I W H L L K I A C T Q S S A R S L V G S S L E G A V T P Q A Y A W L A P D L A E H D H S L
IKK-2 K R Q K E L W N L L K I A C S K - - V R G P V S G S P D - - - S M N A S R L S Q P G Q L M S Q P S T

                         710                 720                 730                 740                 750
IKK-1 S C V V T P Q D G E T S A Q M I E E N L N C L G H L S T I I H E A N E E Q G N S M M N L D W S W L T
IKK-2 A S N S L P E P A K K S E E L V A E A H N L C T L L E N A I Q D T V R E Q D Q S F T A L D W S W L Q

    757         763
IKK-1 E
IKK-2 T E E E E H S C L E Q A S
```

*FIG. 13A*

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
(A) LENGTH: 317 amino acids
(B) TYPE: amino acid
(C) STRANDEDNESS: <Unknown>
(D) TOPOLOGY: linear (xi) SEQUENCE DESCRIPTION: SEQ ID NO: 1:

Met Phe Gln Ala Ala Glu Arg Pro Gln Glu Trp Ala Met Glu Gly Pro
1 5 10 15

Arg Asp Gly Leu Lys Lys Glu Arg Leu Leu Asp Asp Arg His Asp Ser
20 25 30

Gly Leu Asp Ser Met Lys Asp Glu Glu Tyr Glu Gln Met Val Lys Glu
35 40 45

Leu Gln Glu Ile Arg Leu Glu Pro Gln Glu Val Pro Arg Gly Ser Glu
50 55 60

Pro Trp Lys Gln Gln Leu Thr Glu Asp Gly Asp Ser Phe Leu His Leu
65 70 75 80

Ala Ile Ile His Glu Glu Lys Ala Leu Thr Met Glu Val Ile Arg Gln
85 90 95

Val Lys Gly Asp Leu Ala Phe Leu Asn Phe Gln Asn Asn Leu Gln Gln
100 105 110

Thr Pro Leu His Leu Ala Val Ile Thr Asn Gln Pro Glu Ile Ala Glu
115 120 125

Ala Leu Leu Gly Ala Gly Cys Asp Pro Glu Leu Arg Asp Phe Arg Gly
130 135 140

Asn Thr Pro Leu His Leu Ala Cys Glu Gln Gly Cys Leu Ala Ser Val
145 150 155 160

Gly Val Leu Thr Gln Ser Cys Thr Thr Pro His Leu His Ser Ile Leu
165 170 175

Lys Ala Thr Asn Tyr Asn Gly His Thr Cys Leu His Leu Ala Ser Ile
180 185 190

His Gly Tyr Leu Gly Ile Val Glu Leu Leu Val Ser Leu Gly Ala Asp
195 200 205

Val Asn Ala Gln Glu Pro Cys Asn Gly Arg Thr Ala Leu His Leu Ala
210 215 220

Val Asp Leu Gln Asn Pro Asp Leu Val Ser Leu Leu Leu Lys Cys Gly
225 230 235 240

Ala Asp Val Asn Arg Val Thr Tyr Gln Gly Tyr Ser Pro Tyr Gln Leu
245 250 255

Thr Trp Gly Arg Pro Ser Thr Arg Ile Gln Gln Gln Leu Gly Gln Leu
260 265 270

Thr Leu Glu Asn Leu Gln Met Leu Pro Glu Ser Glu Asp Glu Glu Ser
275 280 285

Tyr Asp Thr Glu Ser Glu Phe Thr Glu Phe Thr Glu Asp Glu Leu Pro
290 295 300

Tyr Asp Asp Cys Val Phe Gly Gly Gln Arg Leu Thr Leu
305 310 315

-continued (2) INFORMATION FOR SEQ ID NO: 2:

(i) SEQUENCE CHARACTERISTICS:
(A) LENGTH: 359 amino acids
(B) TYPE: amino acid
(C) STRANDEDNESS: <Unknown>
(D) TOPOLOGY: linear (xi) SEQUENCE DESCRIPTION: SEQ ID NO: 2:

```
Met Ala Gly Val Ala Cys Leu Gly Lys Thr Ala Asp Ala Asp Glu Trp
1               5                   10                  15

Cys Asp Ser Gly Leu Gly Ser Leu Gly Pro Asp Ala Ala Ala Pro Gly
            20                  25                  30

Gly Pro Gly Leu Gly Ala Glu Leu Gly Pro Glu Leu Ser Trp Ala Pro
        35                  40                  45

Leu Val Phe Gly Tyr Val Thr Glu Asp Gly Asp Thr Ala Leu His Leu
    50                  55                  60

Ala Val Ile His Gln His Glu Pro Phe Leu Asp Phe Leu Leu Gly Phe
65                  70                  75                  80

Ser Ala Gly His Glu Tyr Leu Asp Leu Gln Asn Asp Leu Gly Gln Thr
                85                  90                  95

Ala Leu His Leu Ala Ala Ile Leu Gly Glu Ala Ser Thr Val Glu Lys
            100                 105                 110

Leu Tyr Ala Ala Gly Ala Gly Val Leu Val Ala Glu Arg Gly Gly His
        115                 120                 125

Thr Ala Leu His Leu Ala Cys Arg Val Arg Ala His Thr Cys Ala Cys
    130                 135                 140

Val Leu Leu Gln Pro Arg Pro Ser His Pro Arg Asp Ala Ser Asp Thr
145                 150                 155                 160

Tyr Leu Thr Gln Ser Gln Asp Cys Thr Pro Asp Thr Ser His Ala Pro
                165                 170                 175

Ala Ala Val Asp Ser Gln Pro Asn Pro Glu Asn Glu Glu Glu Pro Arg
            180                 185                 190

Asp Glu Asp Trp Arg Leu Gln Leu Glu Ala Glu Asn Tyr Asp Gly His
        195                 200                 205

Thr Pro Leu His Val Ala Val Ile His Lys Asp Ala Glu Met Val Arg
    210                 215                 220

Leu Leu Arg Asp Ala Gly Ala Asp Leu Asn Lys Pro Glu Pro Thr Cys
225                 230                 235                 240

Gly Arg Thr Pro Leu His Leu Ala Val Glu Ala Gln Ala Ala Ser Val
                245                 250                 255

Leu Glu Leu Leu Leu Lys Ala Gly Ala Asp Pro Thr Ala Arg Met Tyr
            260                 265                 270

Gly Gly Arg Thr Pro Leu Gly Ser Ala Leu Leu Arg Pro Asn Pro Ile
        275                 280                 285

Leu Ala Arg Leu Leu Arg Ala His Gly Ala Pro Glu Pro Glu Asp Glu
    290                 295                 300

Asp Asp Lys Leu Ser Pro Cys Ser Ser Ser Gly Ser Asp Ser Asp Ser
305                 310                 315                 320

Asp Asn Arg Asp Glu Gly Asp Glu Tyr Asp Asp Ile Val Val His Ser
                325                 330                 335

Gly Arg Ser Gln Asn Arg Gln Pro Pro Ser Pro Ala Ser Lys Pro Leu
            340                 345                 350

Pro Asp Asp Pro Asn Pro Ala
        355
```

-continued (2) INFORMATION FOR SEQ ID NO: 3:

(i) SEQUENCE CHARACTERISTICS:
(A) LENGTH: 282 amino acids
(B) TYPE: amino acid
(C) STRANDEDNESS: <Unknown>
(D) TOPOLOGY: linear (xi) SEQUENCE DESCRIPTION: SEQ ID NO: 3:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Pro Arg Glu Phe
    210                 215                 220

Ile Val Thr Asp Met Phe Gln Ala Ala Glu Arg Pro Gln Glu Trp Ala
225                 230                 235                 240

Met Glu Gly Pro Arg Asp Gly Leu Lys Lys Glu Arg Leu Leu Asp Asp
                245                 250                 255

Arg His Asp Ser Gly Leu Asp Ser Met Lys Asp Glu Glu Tyr Glu Gln
            260                 265                 270

Met Val Lys Glu Leu Gln Glu Ile Arg Leu
        275                 280
```

(2) INFORMATION FOR SEQ ID NO: 4:

(i) SEQUENCE CHARACTERISTICS:
(A) LENGTH: 272 amino acids
(B) TYPE: amino acid
(C) STRANDEDNESS: <Unknown>
(D) TOPOLOGY: linear (xi) SEQUENCE DESCRIPTION: SEQ ID NO: 4:

```
Met Ser Pro Ile Leu Gly Tyr Trp Lys Ile Lys Gly Leu Val Gln Pro
1               5                   10                  15
```

-continued

```
Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Pro Arg Glu Phe
    210                 215                 220

Ile Val Thr Asp Met Ala Gly Val Ala Cys Leu Gly Lys Thr Ala Asp
225                 230                 235                 240

Ala Asp Glu Trp Cys Asp Ser Gly Leu Gly Ser Leu Gly Pro Asp Ala
                245                 250                 255

Ala Ala Pro Gly Gly Pro Gly Leu Gly Ala Glu Leu Gly Pro Glu Leu
            260                 265                 270
```

(2) INFORMATION FOR SEQ ID NO: 5:

(i) SEQUENCE CHARACTERISTICS:
(A) LENGTH: 282 amino acids
(B) TYPE: amino acid
(C) STRANDEDNESS: <Unknown>
(D) TOPOLOGY: linear (xi) SEQUENCE DESCRIPTION: SEQ ID NO: 5:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110
```

-continued

```
Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Pro Arg Glu Phe
    210                 215                 220

Ile Val Thr Asp Met Phe Gln Ala Ala Glu Arg Pro Gln Glu Trp Ala
225                 230                 235                 240

Met Glu Gly Pro Arg Asp Gly Leu Lys Lys Glu Arg Leu Leu Asp Asp
                245                 250                 255

Arg His Asp Thr Gly Leu Asp Thr Met Lys Asp Glu Glu Tyr Glu Gln
            260                 265                 270

Met Val Lys Glu Leu Gln Glu Ile Arg Leu
        275                 280
```

(2) INFORMATION FOR SEQ ID NO: 6:

(i) SEQUENCE CHARACTERISTICS:
(A) LENGTH: 272 amino acids
(B) TYPE: amino acid
(C) STRANDEDNESS: <Unknown>
(D) TOPOLOGY: linear (xi) SEQUENCE DESCRIPTION: SEQ ID NO: 6:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
```

-continued

```
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Pro Arg Glu Phe
    210                 215                 220

Ile Val Thr Asp Met Ala Gly Val Ala Cys Leu Gly Lys Thr Ala Asp
225                 230                 235                 240

Ala Asp Glu Trp Cys Asp Ala Gly Leu Gly Ala Leu Gly Pro Asp Ala
                245                 250                 255

Ala Ala Pro Gly Gly Pro Gly Leu Gly Ala Glu Leu Gly Pro Glu Leu
            260                 265                 270
```

(2) INFORMATION FOR SEQ ID NO: 7:

(i) SEQUENCE CHARACTERISTICS:
(A) LENGTH: 2251 base pairs
(B) TYPE: nucleic acid
(C) STRANDEDNESS: single
(D) TOPOLOGY: linear (xi) SEQUENCE DESCRIPTION: SEQ ID NO: 7:

```
GGCACGAGGC CCCATGGAGC GGCCCCCGGG GCTGCGGCCG GGCGCGGGCG GGCCCTGGGA     60

GATGCGGGAG CGGCTGGGCA CCGGCGGCTT CGGGAACGTC TGTCTGTACC AGCATCGGGA    120

ACTTGATCTC AAAATAGCAA TTAAGTCTTG TCGCCTAGAG CTAAGTACCA AAAACAGAGA    180

ACGATGGTGC CATGAAATCC AGATTATGAA GAAGTTGAAC CATGCCAATG TTGTAAAGGC    240

CTGTGATGTT CCTGAAGAAT TGAATATTTT GATTCATGAT GTGCCTCTTC TAGCAATGGA    300

ATACTGTTCT GGAGGAGATC TCCGAAAGCT GCTCAACAAA CCAGAAAATT GTTGTGGACT    360

TAAAGAAAGC CAGATACTTT CTTTACTAAG TGATATAGGG TCTGGGATTC GATATTTGCA    420

TGAAAACAAA ATTATACATC GAGATCTAAA ACCTGAAAAC ATAGTTCTTC AGGATGTTGG    480

TGGAAAGATA ATACATAAAA TAATTGATCT GGGATATGCC AAAGATGTTG ATCAAGGAAG    540

TCTGTGTACA TCTTTTGTGG GAACACTGCA GTATCTGGCC CCAGAGCTCT TTGAGAATAA    600

GCCTTACACA GCCACTGTTG ATTATTGGAG CTTTGGGACC ATGGTATTTG AATGTATTGC    660

TGGATATAGG CCTTTTTTGC ATCATCTGCA GCCATTTACC TGGCATGAGA AGATTAAGAA    720

GAAGGATCCA AAGTGTATAT TTGCATGTGA AGAGATGTCA GGAGAAGTTC GGTTTAGTAG    780

CCATTTACCT CAACCAAATA GCCTTTGTAG TTTAATAGTA GAACCCATGG AAAACTGGCT    840

ACAGTTGATG TTGAATTGGG ACCCTCAGCA GAGAGGAGGA CCTGTTGACC TTACTTTGAA    900

GCAGCCAAGA TGTTTTGTAT TAATGGATCA CATTTTGAAT TTGAAGATAG TACACATCCT    960

AAATATGACT TCTGCAAAGA TAATTTCTTT TCTGTTACCA CCTGATGAAA GTCTTCATTC   1020

ACTACAGTCT CGTATTGAGC GTGAAACTGG AATAAATACT GGTTCTCAAG AACTTCTTTC   1080

AGAGACAGGA ATTTCTCTGG ATCCTCGGAA ACCAGCCTCT CAATGTGTTC TAGATGGAGT   1140

TAGAGGCTGT GATAGCTATA TGGTTTATTT GTTTGATAAA AGTAAAACTG TATATGAAGG   1200

GCCATTTGCT TCCAGAAGTT TATCTGATTG TGTAAATTAT ATTGTACAGG ACAGCAAAAT   1260

ACAGCTTCCA ATTATACAGC TGCGTAAAGT GTGGGCTGAA GCAGTGCACT ATGTGTCTGG   1320

ACTAAAAGAA GACTATAGCA GGCTCTTTCA GGGACAAAGG GCAGCAATGT TAAGTCTTCT   1380

TAGATATAAT GCTAACTTAA CAAAAATGAA GAACACTTTG ATCTCAGCAT CACAACAACT   1440

GAAAGCTAAA TTGGAGTTTT TTCACAAAAG CATTCAGCTT GACTTGGAGA GATACAGCGA   1500

GCAGATGACG TATGGGATAT CTTCAGAAAA AATGCTAAAA GCATGGAAAG AAATGGAAGA   1560
```

-continued

```
AAAGGCCATC CACTATGCTG AGGTTGGTGT CATTGGATAC CTGGAGGATC AGATTATGTC   1620

TTTGCATGCT GAAATCATGG AGCTACAGAA GAGCCCCTAT GGAAGACGTC AGGGAGACTT   1680

GATGGAATCT CTGGAACAGC GTGCCATTGA TCTATATAAG CAGTTAAAAC ACAGACCTTC   1740

AGATCACTCC TACAGTGACA GCACAGAGAT GGTGAAAATC ATTGTGCACA CTGTGCAGAG   1800

TCAGGACCGT GTGCTCAAGG AGCGTTTTGG TCATTTGAGC AAGTTGTTGG GCTGTAAGCA   1860

GAAGATTATT GATCTACTCC CTAAGGTGGA AGTGGCCCTC AGTAATATCA AAGAAGCTGA   1920

CAATACTGTC ATGTTCATGC AGGGAAAAAG GCAGAAAGAA ATATGGCATC TCCTTAAAAT   1980

TGCCTGTACA CAGAGTTCTG CCCGCTCTCT TGTAGGATCC AGTCTAGAAG GTGCAGTAAC   2040

CCCTCAAGCA TACGCATGGC TGGCCCCCGA CTTAGCAGAA CATGATCATT CTCTGTCATG   2100

TGTGGTAACT CCTCAAGATG GGGAGACTTC AGCACAAATG ATAGAAGAAA ATTTGAACTG   2160

CCTTGGCCAT TTAAGCACTA TTATTCATGA GGCAAATGAG GAACAGGGCA ATAGTATGAT   2220

GAATCTTGAT TGGAGTTGGT TAACAGAATG A                                 2251
```

(2) INFORMATION FOR SEQ ID NO: 8:

(i) SEQUENCE CHARACTERISTICS:
(A) LENGTH: 2271 base pairs
(B) TYPE: nucleic acid
(C) STRANDEDNESS: single
(D) TOPOLOGY: linear (xi) SEQUENCE DESCRIPTION: SEQ ID NO: 8:

```
ATGAGCTGGT CACCTTCCCT GACAACGCAG ACATGTGGGG CCTGGGAAAT GAAAGAGCGC     60

CTTGGGACAG GGGGATTTGG AAATGTCATC CGATGGCACA ATCAGGAAAC AGGTGAGCAG    120

ATTGCCATCA AGCAGTGCCG GCAGGAGCTC AGCCCCCGGA ACCGAGAGCG GTGGTGCCTG    180

GAGATCCAGA TCATGAGAAG GCTGACCCAC CCCAATGTGG TGGCTGCCCG AGATGTCCCT    240

GAGGGGATGC AGAACTTGGC GCCCAATGAC CTGCCCCTGC TGGCCATGGA GTACTGCCAA    300

GGAGGAGATC TCCGGAAGTA CCTGAACCAG TTTGAGAACT GCTGTGGTCT GCGGGAAGGT    360

GCCATCCTCA CCTTGCTGAG TGACATTGCC TCTGCGCTTA GATACCTTCA TGAAAACAGA    420

ATCATCCATC GGGATCTAAA GCCAGAAAAC ATCGTCCTGC AGCAAGGAGA ACAGAGGTTA    480

ATACACAAAA TTATTGACCT AGGATATGCC AAGGAGCTGG ATCAGGGCAG TCTTTGCACA    540

TCATTCGTGG GGACCCTGCA GTACCTGGCC CCAGAGCTAC TGGAGCAGCA GAAGTACACA    600

GTGACCGTCG ACTACTGGAG CTTCGGCACC CTGGCCTTTG AGTGCATCAC GGGCTTCCGG    660

CCCTTCCTCC CCAACTGGCA GCCCGTGCAG TGGCATTCAA AAGTGCGGCA GAAGAGTGAG    720

GTGGACATTG TTGTTAGCGA AGACTTGAAT GGAACGGTGA AGTTTTCAAG CTCTTTACCC    780

TACCCCAATA ATCTTAACAG TGTCCTGGCT GAGCGACTGG AGAAGTGGCT GCAACTGATG    840

CTGATGTGGC ACCCCCGACA GAGGGGCACG GATCCCACGT ATGGGCCCAA TGGCTGCTTC    900

AAGGCCCTGG ATGACATCTT AAACTTAAAG TTGGTTCATA TCTTGAACAT GGTCACGGGC    960

ACCATCCACA CCTACCCTGT GACAGAGGAT GAGAGTCTGC AGAGCTTGAA GGCCAGAATC   1020

CAACAGGACA CGGGCATCCC AGAGGAGGAC CAGGAGCTGC TGCAGGAAGC GGGCCTGGCG   1080

TTGATCCCCG ATAAGCCTGC CACTCAGTGT ATTTCAGACG GCAAGTTAAA TGAGGGCCAC   1140

ACATTGGACA TGGATCTTGT TTTTCTCTTT GACAACAGTA AAATCACCTA TGAGACTCAG   1200

ATCTCCCCAC GGCCCCAACC TGAAAGTGTC AGCTGTATCC TTCAAGAGCC CAAGAGGAAT   1260

CTCGCCTTCT TCCACCTGAG GAAGGTGTGG GGCCAGGTCT GGCACAGCAT CCAGACCCTG   1320
```

-continued

```
AAGGAAGATT GCAACCGGCT GCAGCAGGGA CAGCGAGCCG CCATGATGAA TCTCCTCCGA   1380

AACAACAGCT GCCTCTCCAA AATGAAGAAT TCCATGGCTT CCATGTCTCA GCAGCTCAAG   1440

GCCAAGTTGG ATTTCTTCAA AACCAGCATC CAGATTGACC TGGAGAAGTA CAGCGAGCAA   1500

ACCGAGTTTG GGATCACATC AGATAAACTG CTGCTGGCCT GGAGGGAAAT GGAGCAGGCT   1560

GTGGAGCTCT GTGGGCGGGA GAACGAAGTG AAACTCCTGG TAGAACGGAT GATGGCTCTG   1620

CAGACCGACA TTGTGGACTT ACAGAGGAGC CCCATGGGCC GGAAGCAGGG GGGAACGCTG   1680

GACGACCTAG AGGAGCAAGC AAGGGAGCTG TACAGGAGAC TAAGGGAAAA ACCTCGAGAC   1740

CAGCGAACTG AGGGTGACAG TCAGGAAATG GTACGGCTGC TGCTTCAGGC AATTCAGAGC   1800

TTCGAGAAGA AAGTGCGAGT GATCTATACG CAGCTCAGTA AAACTGTGGT TTGCAAGCAG   1860

AAGGCGCTGG AACTGTTGCC CAAGGTGGAA GAGGTGGTGA GCTTAATGAA TGAGGATGAG   1920

AAGACTGTTG TCCGGCTGCA GGAGAAGCGG CAGAAGGAGC TCTGGAATCT CCTGAAGATT   1980

GCTTGTAGCA AGGTCCGTGG TCCTGTCAGT GGAAGCCCGG ATAGCATGAA TGCCTCTCGA   2040

CTTAGCCAGC CTGGGCAGCT GATGTCTCAG CCCTCCACGG CCTCCAACAG CTTACCTGAG   2100

CCAGCCAAGA AGAGTGAAGA ACTGGTGGCT GAAGCACATA ACCTCTGCAC CCTGCTAGAA   2160

AATGCCATAC AGGACACTGT GAGGGAACAA GACCAGAGTT TCACGGCCCT AGACTGGAGC   2220

TGGTTACAGA CGGAAGAAGA AGAGCACAGC TGCCTGGAGC AGGCCTCATG A            2271
```

(2) INFORMATION FOR SEQ ID NO: 9:

(i) SEQUENCE CHARACTERISTICS:
(A) LENGTH: 756 amino acids
(B) TYPE: amino acid
(C) STRANDEDNESS: <Unknown>
(D) TOPOLOGY: linear (xi) SEQUENCE DESCRIPTION: SEQ ID NO: 9:

```
Met Ser Trp Ser Pro Ser Leu Thr Thr Gln Thr Cys Gly Ala Trp Glu
1               5                   10                  15

Met Lys Glu Arg Leu Gly Thr Gly Gly Phe Gly Asn Val Ile Arg Trp
            20                  25                  30

His Asn Gln Glu Thr Gly Glu Gln Ile Ala Ile Lys Gln Cys Arg Gln
        35                  40                  45

Glu Leu Ser Pro Arg Asn Arg Glu Arg Trp Cys Leu Glu Ile Gln Ile
    50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
        115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Ser Leu Cys Thr Ser Phe Val Gly Thr Leu Gln Tyr Leu Ala Pro Glu
            180                 185                 190
```

-continued

```
Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
    210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Thr Val Lys Phe Ser
                245                 250                 255

Ser Ser Leu Pro Tyr Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Thr Tyr Gly Pro Asn Gly Cys Phe Lys Ala Leu Asp
    290                 295                 300

Asp Ile Leu Asn Leu Lys Leu Val His Ile Leu Asn Met Val Thr Gly
305                 310                 315                 320

Thr Ile His Thr Tyr Pro Val Thr Glu Asp Glu Ser Leu Gln Ser Leu
                325                 330                 335

Lys Ala Arg Ile Gln Gln Asp Thr Gly Ile Pro Glu Glu Asp Gln Glu
            340                 345                 350

Leu Leu Gln Glu Ala Gly Leu Ala Leu Ile Pro Asp Lys Pro Ala Thr
        355                 360                 365

Gln Cys Ile Ser Asp Gly Lys Leu Asn Glu Gly His Thr Leu Asp Met
    370                 375                 380

Asp Leu Val Phe Leu Phe Asp Asn Ser Lys Ile Thr Tyr Glu Thr Gln
385                 390                 395                 400

Ile Ser Pro Arg Pro Gln Pro Glu Ser Val Ser Cys Ile Leu Gln Glu
                405                 410                 415

Pro Lys Arg Asn Leu Ala Phe Phe His Leu Arg Lys Val Trp Gly Gln
            420                 425                 430

Val Trp His Ser Ile Gln Thr Leu Lys Glu Asp Cys Asn Arg Leu Gln
        435                 440                 445

Gln Gly Gln Arg Ala Ala Met Met Asn Leu Leu Arg Asn Asn Ser Cys
    450                 455                 460

Leu Ser Lys Met Lys Asn Ser Met Ala Ser Met Ser Gln Gln Leu Lys
465                 470                 475                 480

Ala Lys Leu Asp Phe Phe Lys Thr Ser Ile Gln Ile Asp Leu Glu Lys
                485                 490                 495

Tyr Ser Glu Gln Thr Glu Phe Gly Ile Thr Ser Asp Lys Leu Leu Leu
            500                 505                 510

Ala Trp Arg Glu Met Glu Gln Ala Val Glu Leu Cys Gly Arg Glu Asn
        515                 520                 525

Glu Val Lys Leu Leu Val Glu Arg Met Met Ala Leu Gln Thr Asp Ile
    530                 535                 540

Val Asp Leu Gln Arg Ser Pro Met Gly Arg Lys Gln Gly Gly Thr Leu
545                 550                 555                 560

Asp Asp Leu Glu Glu Gln Ala Arg Glu Leu Tyr Arg Arg Leu Arg Glu
                565                 570                 575

Lys Pro Arg Asp Gln Arg Thr Glu Gly Asp Ser Gln Glu Met Val Arg
            580                 585                 590

Leu Leu Leu Gln Ala Ile Gln Ser Phe Glu Lys Lys Val Arg Val Ile
        595                 600                 605
```

-continued

Tyr Thr Gln Leu Ser Lys Thr Val Val Cys Lys Gln Lys Ala Leu Glu
    610                 615                 620

Leu Leu Pro Lys Val Glu Glu Val Val Ser Leu Met Asn Glu Asp Glu
625                 630                 635                 640

Lys Thr Val Val Arg Leu Gln Glu Lys Arg Gln Lys Glu Leu Trp Asn
                645                 650                 655

Leu Leu Lys Ile Ala Cys Ser Lys Val Arg Gly Pro Val Ser Gly Ser
            660                 665                 670

Pro Asp Ser Met Asn Ala Ser Arg Leu Ser Gln Pro Gly Gln Leu Met
        675                 680                 685

Ser Gln Pro Ser Thr Ala Ser Asn Ser Leu Pro Glu Pro Ala Lys Lys
    690                 695                 700

Ser Glu Glu Leu Val Ala Glu Ala His Asn Leu Cys Thr Leu Leu Glu
705                 710                 715                 720

Asn Ala Ile Gln Asp Thr Val Arg Glu Gln Asp Gln Ser Phe Thr Ala
                725                 730                 735

Leu Asp Trp Ser Trp Leu Gln Thr Glu Glu Glu Glu His Ser Cys Leu
            740                 745                 750

Glu Gln Ala Ser
        755

(2) INFORMATION FOR SEQ ID NO: 10:

(i) SEQUENCE CHARACTERISTICS:
(A) LENGTH: 745 amino acids
(B) TYPE: amino acid
(C) STRANDEDNESS: <Unknown>
(D) TOPOLOGY: linear (xi) SEQUENCE DESCRIPTION: SEQ ID NO: 10:

Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Cys Leu Tyr
            20                  25                  30

Gln His Arg Glu Leu Asp Leu Lys Ile Ala Ile Lys Ser Cys Arg Leu
        35                  40                  45

Glu Leu Ser Thr Lys Asn Arg Glu Arg Trp Cys His Glu Ile Gln Ile
    50                  55                  60

Met Lys Lys Leu Asn His Ala Asn Val Val Lys Ala Cys Asp Val Pro
65                  70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
        195                 200                 205

-continued

```
Thr Met Val Phe Glu Cys Ile Ala Gly Tyr Arg Pro Phe Leu His His
    210                 215                 220

Leu Gln Pro Phe Thr Trp His Glu Lys Ile Lys Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Ile Val Glu Pro Met
            260                 265                 270

Glu Asn Trp Leu Gln Leu Met Leu Asn Trp Asp Pro Gln Gln Arg Gly
        275                 280                 285

Gly Pro Val Asp Leu Thr Leu Lys Gln Pro Arg Cys Phe Val Leu Met
    290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Pro Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
    370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
    450                 455                 460

Met Lys Asn Thr Leu Ile Ser Ala Ser Gln Gln Leu Lys Ala Lys Leu
465                 470                 475                 480

Glu Phe Phe His Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
        515                 520                 525

Tyr Leu Glu Asp Gln Ile Met Ser Leu His Ala Glu Ile Met Glu Leu
    530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Ser
                565                 570                 575

Asp His Ser Tyr Ser Asp Ser Thr Glu Met Val Lys Ile Ile Val His
            580                 585                 590

Thr Val Gln Ser Gln Asp Arg Val Leu Lys Glu Arg Phe Gly His Leu
        595                 600                 605

Ser Lys Leu Leu Gly Cys Lys Gln Lys Ile Ile Asp Leu Leu Pro Lys
    610                 615                 620
```

-continued

Val Glu Val Ala Leu Ser Asn Ile Lys Glu Ala Asp Asn Thr Val Met
625 630 635 640

Phe Met Gln Gly Lys Arg Gln Lys Glu Ile Trp His Leu Leu Lys Ile
645 650 655

Ala Cys Thr Gln Ser Ser Ala Arg Ser Leu Val Gly Ser Ser Leu Glu
660 665 670

Gly Ala Val Thr Pro Gln Ala Tyr Ala Trp Leu Ala Pro Asp Leu Ala
675 680 685

Glu His Asp His Ser Leu Ser Cys Val Val Thr Pro Gln Asp Gly Glu
690 695 700

Thr Ser Ala Gln Met Ile Glu Glu Asn Leu Asn Cys Leu Gly His Leu
705 710 715 720

Ser Thr Ile Ile His Glu Ala Asn Glu Glu Gln Gly Asn Ser Met Met
725 730 735

Asn Leu Asp Trp Ser Trp Leu Thr Glu
740 745

(2) INFORMATION FOR SEQ ID NO: 11:

(i) SEQUENCE CHARACTERISTICS:
(A) LENGTH: 22 amino acids
(B) TYPE: amino acid
(C) STRANDEDNESS: <Unknown>
(D) TOPOLOGY: linear (xi) SEQUENCE DESCRIPTION: SEQ ID NO: 11:

Cys Lys Lys Glu Arg Leu Leu Asp Asp Arg His Asp Ser Gly Leu Asp
1 5 10 15

Ser Met Lys Asp Glu Glu
20

(2) INFORMATION FOR SEQ ID NO: 12:

(i) SEQUENCE CHARACTERISTICS:
(A) LENGTH: 22 amino acids
(B) TYPE: amino acid
(C) STRANDEDNESS: <Unknown>
(D) TOPOLOGY: linear (xi) SEQUENCE DESCRIPTION: SEQ ID NO: 12:

Cys Lys Lys Glu Arg Leu Leu Asp Asp Arg His Asp Thr Gly Leu Asp
1 5 10 15

Thr Met Lys Asp Glu Glu
20

(2) INFORMATION FOR SEQ ID NO: 13:

(i) SEQUENCE CHARACTERISTICS:
(A) LENGTH: 19 amino acids
(B) TYPE: amino acid
(C) STRANDEDNESS: <Unknown>
(D) TOPOLOGY: linear (ix) FEATURE:
(A) NAME/KEY: Modified-site
(B) LOCATION: 10
(D) OTHER INFORMATION: /note= "Where Xaa is a Phosphate Ester of Threonine"

(xi) SEQUENCE DESCRIPTION: SEQ ID NO: 13:

Asp Leu Thr Gly Gly Pro Glu Val Ala Xaa Pro Glu Ser Glu Glu Ala
1 5 10 15

Phe Leu Pro

-continued (2) INFORMATION FOR SEQ ID NO: 14:

(i) SEQUENCE CHARACTERISTICS:
(A) LENGTH: 19 amino acids
(B) TYPE: amino acid
(C) STRANDEDNESS: <Unknown>
(D) TOPOLOGY: linear (xi) SEQUENCE DESCRIPTION: SEQ ID NO: 14:

Cys Pro Thr Asn Ser Ala Leu Asn Tyr Leu Lys Ser Pro Ile Thr Thr
1 5 10 15

Ser Pro Ser (2) INFORMATION FOR SEQ ID NO: 15:

(i) SEQUENCE CHARACTERISTICS:
(A) LENGTH: 15 amino acids
(B) TYPE: amino acid
(C) STRANDEDNESS: <Unknown>
(D) TOPOLOGY: linear (xi) SEQUENCE DESCRIPTION: SEQ ID NO: 15:

Cys Asn Ser Asp Leu Leu Thr Ser Pro Asp Val Gly Leu Leu Lys
1 5 10 15

(2) INFORMATION FOR SEQ ID NO: 16:

(i) SEQUENCE CHARACTERISTICS:
(A) LENGTH: 15 amino acids
(B) TYPE: amino acid
(C) STRANDEDNESS: <Unknown>
(D) TOPOLOGY: linear (xi) SEQUENCE DESCRIPTION: SEQ ID NO: 16:

Cys Val Gly Leu Leu Lys Leu Ala Ser Pro Glu Leu Glu Arg Leu
1 5 10 15

(2) INFORMATION FOR SEQ ID NO: 17:

(i) SEQUENCE CHARACTERISTICS:
(A) LENGTH: 8 amino acids
(B) TYPE: amino acid
(C) STRANDEDNESS: <Unknown>
(D) TOPOLOGY: linear (xi) SEQUENCE DESCRIPTION: SEQ ID NO: 17:

Ile Ile Asp Leu Gly Tyr Ala Lys
1 5

(2) INFORMATION FOR SEQ ID NO: 18:

(i) SEQUENCE CHARACTERISTICS:
(A) LENGTH: 9 amino acids
(B) TYPE: amino acid
(C) STRANDEDNESS: <Unknown>
(D) TOPOLOGY: linear (xi) SEQUENCE DESCRIPTION: SEQ ID NO: 18:

Val Glu Val Ala Leu Ser Asn Ile Lys
1 5

(2) INFORMATION FOR SEQ ID NO: 19:

(i) SEQUENCE CHARACTERISTICS:
(A) LENGTH: 8 amino acids
(B) TYPE: amino acid

-continued (C) STRANDEDNESS: <Unknown>
(D) TOPOLOGY: linear (xi) SEQUENCE DESCRIPTION: SEQ ID NO: 19:

Ser Ile Gln Leu Asp Leu Glu Arg
1 5

(2) INFORMATION FOR SEQ ID NO: 20:

(i) SEQUENCE CHARACTERISTICS:
(A) LENGTH: 7 amino acids
(B) TYPE: amino acid
(C) STRANDEDNESS: <Unknown>
(D) TOPOLOGY: linear (xi) SEQUENCE DESCRIPTION: SEQ ID NO: 20:

Ala Leu Glu Leu Leu Pro Lys
1 5

(2) INFORMATION FOR SEQ ID NO: 21:

(i) SEQUENCE CHARACTERISTICS:
(A) LENGTH: 8 amino acids
(B) TYPE: amino acid
(C) STRANDEDNESS: <Unknown>
(D) TOPOLOGY: linear (xi) SEQUENCE DESCRIPTION: SEQ ID NO: 21:

Val Ile Tyr Thr Gln Leu Ser Lys
1 5

(2) INFORMATION FOR SEQ ID NO: 22:

(i) SEQUENCE CHARACTERISTICS:
(A) LENGTH: 11 amino acids
(B) TYPE: amino acid
(C) STRANDEDNESS: <Unknown>
(D) TOPOLOGY: linear (xi) SEQUENCE DESCRIPTION: SEQ ID NO: 22:

Leu Leu Leu Gln Ala Ile Gln Ser Phe Glu Lys
1 5 10

(2) INFORMATION FOR SEQ ID NO: 23:

(i) SEQUENCE CHARACTERISTICS:
(A) LENGTH: 11 amino acids
(B) TYPE: amino acid
(C) STRANDEDNESS: <Unknown>
(D) TOPOLOGY: linear (xi) SEQUENCE DESCRIPTION: SEQ ID NO: 23:

Leu Gly Thr Gly Gly Phe Gly Asn Val Ile Arg
1 5 10

(2) INFORMATION FOR SEQ ID NO: 24:

(i) SEQUENCE CHARACTERISTICS:
(A) LENGTH: 9 amino acids
(B) TYPE: amino acid
(C) STRANDEDNESS: <Unknown>
(D) TOPOLOGY: linear (xi) SEQUENCE DESCRIPTION: SEQ ID NO: 24:

Ala Leu Asp Asp Ile Leu Asn Leu Lys
1 5

-continued

```
(2) INFORMATION FOR SEQ ID NO: 25:

    (i) SEQUENCE CHARACTERISTICS:
        (A) LENGTH: 15 amino acids
        (B) TYPE: amino acid
        (C) STRANDEDNESS: <Unknown>
        (D) TOPOLOGY: linear

   (xi) SEQUENCE DESCRIPTION: SEQ ID NO: 25:

Asp Leu Lys Pro Glu Asn Ile Val Leu Gln Gln Gly Glu Gln Arg
1               5                   10                  15
```

STIMULUS-INDUCIBLE PROTEIN KINASE COMPLEX AND METHODS OF USE THEREFOR

CROSS-REFERENCE TO PRIOR APPLICATION

This is a divisional application of Ser. No. 08/910,820 filed Aug. 13, 1997 now U.S. Pat. No. 6,258,579, which is a continuation-in-part of U.S. patent application No. 08/697,393, filed Aug. 26, 1996 now U.S. Pat. No. 5,972,674.

TECHNICAL FIELD

The present invention relates generally to compositions and methods useful for the study of cascades leading to the activation of nuclear factor κB (NF-κB) and for treating diseases associated with such pathways. The invention is more particularly related to a stimulus-inducible IκB kinase (IKK) signalsome, component IκB kinases and variants of such kinases. The present invention is also related to the use of a stimulus-inducible IKK signalsome or IκB kinase to identify antibodies and other agents that inhibit or activate signal transduction via the NF-κB pathway.

BACKGROUND OF THE INVENTION

Transcription factors of the NFκB/Rel family are critical regulators of genes involved in inflammation, cell proliferation and apoptosis (for reviews, see Verma et al., *Genes Dev.* 9:2723–35, 1995; Siebenlist, *Biochim. Biophys. Acta* 1332:7–13, 1997; Baeuerle and Henkel, *Ann. Rev. Immunol.* 12:141–79, 1994; Barnes and Karin, *New Engl. J. Med.* 336, 1066–71, 1997; Baeuerle and Baltimore, *Cell* 87:13–20, 1996; Grilli et al., *NF-kB and Rel: Participants in a multiform transcriptional regulatory system* (Academic Press, Inc., 1993), vol. 143; Baichwal and Baeuerle, *Curr. Biol.* 7:94–96, 1997). The prototype member of the family, NFκB, is composed of a dimer of p50 NFκB and p65 RelA (Baeuerle and Baltimore, *Cell* 53:211–17, 1988; Baeuerle and Baltimore, *Genes Dev.* 3:1689–98, 1989). NF-κB plays a pivotal role in the highly specific pattern of gene expression observed for immune, inflammatory and acute phase response genes, including interleukin 1, interleukin 8, tumor necrosis factor and certain cell adhesion molecules.

Like other members of the Rel family of transcriptional activators, NF-κB is sequestered in an inactive form in the cytoplasm of most cell types. A variety of extracellular stimuli including mitogens, cytokines, antigens, stress inducing agents, UV light and viral proteins initiate a signal transduction pathway that ultimately leads to NF-κB release and activation. Thus, inhibitors and activators of the signal transduction pathway may be used to alter the level of active NF-κB, and have potential utility in the treatment of diseases associated with NF-κB activation.

Activation of NFκB in response to each of these stimuli is controlled by an inhibitory subunit, IκB, which retains NFκB in the cytoplasm. IκB proteins, of which there are six known members, each contain 5–7 ankyrin-like repeats required for association with the NFκB/Rel dimer and for inhibitory activity (see Beg et al., *Genes Dev.* 7, 2064–70, 1993; Gilmore and Morin, *Trends Genet.* 9, 427–33, 1993; Diaz-Meco et al., *Mol. Cell. Biol.* 13:4770–75, 1993; Haskill et al., *Cell* 65:1281–89, 1991). IκB proteins include IκBα and IκBβ.

NFκB activation involves the sequential phosphorylation, ubiquitination, and degradation of IκB. Phosphorylation of IκB is highly specific for target residues. For example, phosphorylation of the IκB protein IκBα takes place at serine residues S32 and S36, and phosphorylation of IκBβ occurs at serine residues S19 and S23. The choreographed series of modification and degradation steps results in nuclear import of transcriptionally active NFκB due to the exposure of a nuclear localization signal on NFκB that was previously masked by IκB (Beg et al., *Genes Dev.* 6:1899–1913, 1992). Thus, NFκB activation is mediated by a signal transduction cascade that includes one or more specific IκB kinases, a linked series of E1, E2 and E3 ubiquitin enzymes, the 26S proteasome, and the nuclear import machinery. The phosphorylation of IκB is a critical step in NF-κB activation, and the identification of an IκB kinase, as well as proteins that modulate its kinase activity, would further the understanding of the activation process, as well as the development of therapeutic methods.

Several protein kinases have been found to phosphorylate IκB in vitro, including protein kinase A (Ghosh and Baltimore, *Nature* 344:678–82, 1990), protein kinase C (Ghosh and Baltimore, *Nature* 344:678–82, 1990) and double stranded RNA-dependent protein kinase (Kumar et al., *Proc. Natl. Acad. Sci. USA* 91:6288–92, 1994). Constitutive phosphorylation of IκBα by casein kinase II has also been observed (see Barroga et al., *Proc. Natl. Acad. Sci. USA* 92:7637–41, 1995). None of these kinases, however appear to be responsible for in vivo activation of NF-κB. For example, phosphorylation of IκBα in vitro by protein kinase A and protein kinase C prevent its association with NF-κB, and phosphorylation by double-stranded RNA-dependent protein kinase results in dissociation of NF-κB. Neither of these conform to the effect of phosphorylation in vivo, where IκBα phosphorylation at S32 and S36 does not result in dissociation from NF-κB.

Other previously unknown proteins with IκB kinase activity have been reported, but these proteins also do not appear to be significant activators in vivo. A putative IκBα kinase was identified by Kuno et al., *J. Biol. Chem.* 270:27914–27919, 1995, but that kinase appears to phosphorylate residues in the C-terminal region of IκBα, rather than the S32 and S36 residues known to be important for in vivo regulation. Diaz-Meco et al., *EMBO J.* 13:2842–2848, 1994 also identified a 50 kD IκB kinase, with uncharacterized phosphorylation sites. Schouten et al., *EMBO J.* 16:3133–44, 1997 identified $p90^{rski}$ as a putative IκBα kinase; however, $p90^{rski}$ is only activated by TPA and phosphorylates IκBα only on Ser32, which is insufficient to render IκBα a target for ubiquitination. Finally, Chen et al, *Cell* 84:853–862, 1996 identified a kinase that phosphorylates IκBα, but that kinase was identified using a non-physiological inducer of IκBα kinase activity and requires the addition of exogenous factors for in vitro phosphorylation.

Accordingly, there is a need in the art for an IκB kinase that possesses the substrate specificity and other properties of the in vivo kinase. There is also a need for improved methods for modulating the activity of proteins involved in activation of NF-κand for treating diseases associated with NF-κcB activation. The present invention fulfills these needs and further provides other related advantages.

SUMMARY OF THE INVENTION

Briefly stated, the present invention provides compositions and methods employing a large, multi-subunit IKK signalsome, or a component or variant thereof. In one aspect, the present invention provides an IKK signalsome capable of specifically phosphorylating IκBα at residues S32 and S36, and IκKβ at residues 19 and 23, without the addition of exogenous cofactors.

In a further related aspect, a polypeptide comprising a component of an IKK signalsome, or a variant of such a component, is provided, wherein the component has a sequence recited in SEQ ID NO:9. An isolated DNA molecule and recombinant expression vector encoding such a polypeptide, as well as a transfected host cell, are also provided.

In another aspect, methods for preparing an IKK signalsome are provided, comprising combining components of an IKK signalsome in a suitable buffer.

In yet another aspect, methods are provided for phosphorylating a substrate of an IKK signalsome, comprising contacting a substrate with an IKK signalsome or a component thereof, and thereby phosphorylating the substrate.

In a further aspect, the present invention provides a method for screening for an agent that modulates IKK signalsome activity, comprising: (a) contacting a candidate agent with an IKK signalsome, wherein the step of contacting is carried out under conditions and for a time sufficient to allow the candidate agent and the IKK signalsome to interact; and (b) subsequently measuring the ability of the candidate agent to modulate IKK signalsome activity.

Within a related aspect, the present invention provides methods for screening for an agent that modulates IKK signalsome activity, comprising: (a) contacting a candidate agent with a polypeptide comprising a component of an IKK signalsome as described above, wherein the step of contacting is carried out under conditions and for a time sufficient to allow the candidate agent and the polypeptide to interact; and (b) subsequently measuring the ability of the candidate agent to modulate the ability of the polypeptide to phosphorylate an IκB protein.

In another aspect, an antibody is provided that binds to a component (e.g., IKK-1 and/or IKK-2) of an IKK signalsome, where the component is capable of phosphorylating IκBα.

In further aspects, the present invention provides methods for modulating NF-κB activity in a patient, comprising administering to a patient an agent that modulates IκB kinase activity in combination with a pharmaceutically acceptable carrier. Methods are also provided for treating a patient afflicted with a disorder associated with the activation of IKK signalsome, comprising administering to a patient a therapeutically effective amount of an agent that modulates IκB kinase activity in combination with a pharmaceutically acceptable carrier.

In yet another aspect, a method for detecting IKK signalsome activity in a sample is provided, comprising: (a) contacting a sample with an antibody that binds to an IKK signalsome under conditions and for a time sufficient to allow the antibody to immunoprecipitate an IKK signalsome; (b) separating immunoprecipitated material from the sample; and (c) determining the ability of the immunoprecipitated material to specifically phosphorylate an IκB protein with in vivo specificity. Within one such embodiment, the ability of the immunoprecipitated material to phosphorylate IκBα at residues S32 and/or S36 is determined.

In a related aspect, a kit for detecting IKK signalsome activity in a sample is provided, comprising an antibody that binds to an IKK signalsome in combination with a suitable buffer.

In a further aspect, the present invention provides a method for identifying an upstream kinase in the NF-κB signal transduction cascade, comprising evaluating the ability of a candidate upstream kinase to phosphorylate an IKK signalsome, a component thereof or a variant of such a component.

A method for identifying a component of an IKK signalsome is also provided, comprising: (a) isolating an IKK signalsome; (b) separating the signalsome into components, and (c) obtaining a partial sequence of a component.

In yet another aspect, a method is provided for preparing an IKK signalsome from a biological sample, comprising: (a) separating a biological sample into two or more fractions; and (b) monitoring IκB kinase activity in the fractions.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1A shows the recruitment of IκBα into a high molecular weight complex upon stimulation. Cytoplasmic extracts of either unstimulated or PMA(50 ng/ml)- and PHA(1 μg/ml)-stimulated (10 min) Jurkat cells were fractionated on a gel filtration column. IκBα was visualized by immunoblot analysis. The upper panel shows the elution profile of unstimulated cells, and the lower panel shows the elution profile of PMA/PHA-stimulated cells. Molecular weight standards are indicated by arrows on the top.

FIG. 1B shows that the stimulus-dependent IκBα kinase activity chromatographs as a high molecular weight complex, $M_r$ 500–700 kDa. Whole cell extract of TNFα-stimulated (20 ng/ml, 7 min) HeLa S3 cells was fractionated on a Superdex 200 gel filtration column and monitored for IκBα kinase activity. Phosphorylation of the GST IκBα 1–54 (wildtype) substrate is indicated by an arrow to the right. Molecular weight standards are indicated by arrows on the top.

FIG. 1C illustrates the identification of proteins that co-chromatograph with the IKK signalsome. IKK signalsome was partially purified from extracts of TNFα-stimulated HeLa S3 cells by sequential fractionation on a Q Sepharose, Superdex 200, Mono Q, and Phenyl Superose columns. Phenyl Superose fractions containing the peak of IKK signalsome activity were subjected to western blot analysis using several different antibodies as indicated to the left of each respective panel. The level of IKK signalsome activity is indicated in the upper shaded area by increasing number of (+)'s.

FIG. 4A shows the results employing an extract from cells that were not treated with TNFα, and FIG. 4B shows the results when the cells were treated with TNFα.

In FIG. 8A, the upper panel presents a time course for the induction of signalsome activity. Anti MKP-1 immune precipitates from extracts of HeLa S3 cells stimulated with TNFα (20 ng/ml) for the indicated times, were assayed for IKK signalsome activity by standard immune complex kinase assays. 4 μg of either GST IκBα 1–54 WT (wildtype) or the GST IκBα 1–54 S32/36 to T mutant (S>T) were used as the substrates. In the lower panel, HeLa cell extracts prepared as described in the upper panel were examined by western blot analysis for IκBα degradation. IκBα supershifting phosphorylation can be seen after 3 and 5 minutes of stimulation followed by the disappearance of IκBα.

FIG. 8B illustrates the stimulus-dependent activation of IKK signalsome, which is blocked by TPCK. Anti-MKP-1 immunoprecipitates from cell extracts of HeLa S3 cells either stimulated for 7 min with TNFα (20 ng/ml, lane 2 and 6), IL-1 (10 ng/ml, lane 3), PMA (50 ng/ml, lane 4) or pretreated for 30 min with TPCK (15 μM, lane 7) prior to TNFα-induction were examined for IKK signalsome activity. GST IκBα 1–54 WT (4 μg) was used as a substrate.

FIG. 8C illustrates the ability of IKK signalsome to specifically phosphorylate serines 32 and 36 of the IκBα holoprotein in the context of a RelA:IκBα complex. Anti-MKP-1 immunoprecipitates from cell extracts of HeLa S3 cells stimulated with TNFα (20 ng/ml, 7 min) were examined for their ability to phosphorylate baculoviral expressed RelA:IκBα complex containing either the IκBα WT (lane 3) or IκBα S32/36 to A mutant (lane 4) holoprotein. The specific substrates used are indicated on the top. Positions of the phosphorylated substrates are indicated by arrows to the left of the panel.

FIG. 12A shows part of the mass spectrum of the unseparated mixture of tryptic peptides resulting from in-gel digestion of the IKK-2 band in FIG. 11B. FIG. 12B shows a tandem mass spectrum of the peak at m/z 645.2.

FIG. 13A illustrates the amino acid sequence of IKK-1 and IKK-2. Symbols: arrows, boundaries of the kinase domain; underlined, peptide sequences identified by nanoelectrospray mass spectrometry; asterisks, indicates leucines comprising the leucine zipper motif; bold face, indicate amino acid identities conserved between IKK-1 and IKK-2; highlighted box, Helix-loop-helix domain; dashes, a gap inserted to optimize alignment.

In FIG. 15A, HA-tagged IKK-1 and Flag-tagged IKK-2 were in vitro translated in wheat germ lysates either separately or in combination, as indicated. The programmed translation mix was then subjected to immunoprecipitation using the indicated antibody. The samples were run on SDS-PAGE and subjected to autoradiography. In FIG. 15B, HA-tagged IKK-1 and Flag-tagged IKK-2 were in vitro translated in rabbit reticulocyte lysates either separately or in combination, as indicated. The programmed translation mix was then subjected to immunoprecipitation using the indicated antibody. The samples were rur on SDS-PAGE and subjected to autoradiography. The results show that IKK-1 and IKK-2 coprecipitate when translated in rabbit reticulocyte lysates.

DETAILED DESCRIPTION OF THE INVENTION

As noted above, the present invention is generally directed to compositions and methods for modulating (i.e., stimulating or inhibiting) signal transduction leading to NF-κB activation. In particular, the present invention is directed to compositions comprising an IκB kinase (IKK) signalsome (also referred to herein as a "stimulus-inducible IκB kinase complex" or "IκB kinase complex") that is capable of stimulus-dependent phosphorylation of IκBα and IκBβ on the two N-terminal serine residues critical for the subsequent ubiquitination and degradation in vivo. Such stimulus-dependent phosphorylation may be achieved without the addition of exogenous cofactors. In particular, an IKK signalsome specifically phosphorylates IκBα (SEQ ID NO:1) at residues S32 and S36 and phosphorylates IκBβ (SEQ ID NO:2) at residues S19 and S23. The present invention also encompasses compositions that contain one or more components of such an IKK signalsome, or variants of such components. Preferred components, referred to herein as "IKK signalsome kinases" "IκB kinases" or IKKs) are kinases that, when incorporated into an IKK signalsome, are capable of phosphorylating IκBα at S32 and S36. Particularly preferred components are IKK-1 (SEQ ID NO:10) and IKK-2 (SEQ ID NO:9).

An IKK signalsome and/or IκB kinase may generally be used for phosphorylating a substrate (i.e., an IκB, such as IκBα, or a portion or variant thereof that can be phosphorylated at those residues that are phosphorylated in vivo) and for identifying modulators of IκB kinase activity. Such modulators and methods employing them for modulating IκBα kinase activity, in vivo and/or in vitro, are also encompassed by the present invention. In general, compositions that inhibit IκB kinase activity may inhibit IκB phosphorylation, or may inhibit the activation of an IκB kinase and/or IKK signalsome.

Figure 3A:
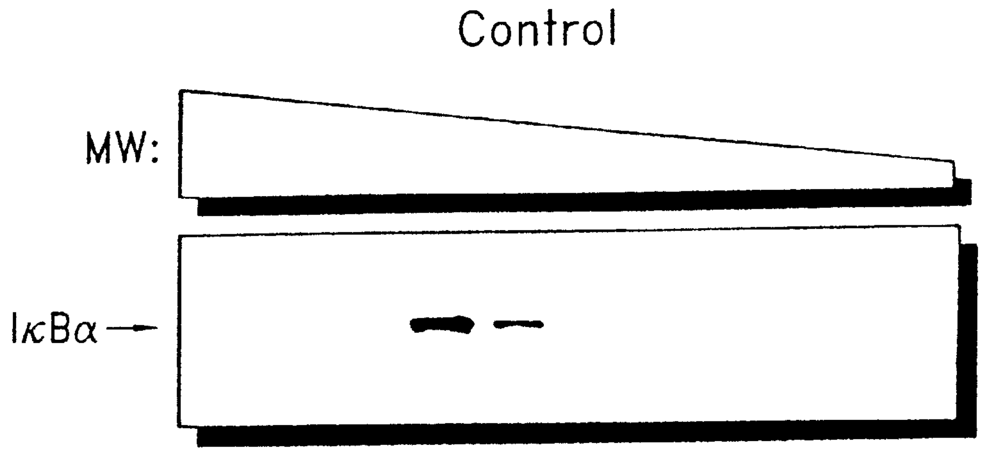
FIGS. 3A and 3B are autoradiograms that show the results of a Western blot analysis of the levels of IκBα in HeLa S3 cytoplasmic extracts following gel filtration. The extracts were prepared from cells that were (FIG. 3B) and were not (FIG. 3A) exposed to TNFα.
Figure 3B:
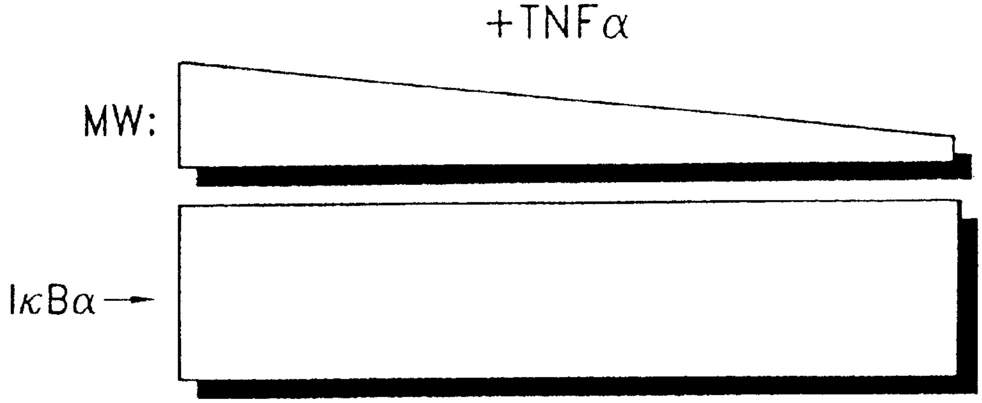

An IKK signalsome has several distinctive properties. Such a complex is stable (i.e., its components remain associated following purification as described herein) and has a high-molecular weight (about 500–700 kD, as determined by gel filtration chromatography). As shown in FIGS. 3 (A and B) and 4 (A and B), IκB kinase activity of an IKK signalsome is "stimulus-inducible" in that it is stimulated by TNFα (i.e., treatment of cells with TNFα results in increased IκB kinase activity and IκB degradation) and/or by one or more other inducers of NF-κB, such as IL-1, LPS, TPA, UV irradiation, antigens, viral proteins and stress-inducing agents. The kinetics of stimulation by TNFα correspond to those found in vivo. IκB kinase activity of an IKK signalsome is also specific for S32 and S36 of IκBα. As shown in FIGS. 5 (A and B) and 6 (A and B), an IKK signalsome is capable of phosphorylating a polypeptide having the N-terminal sequence of IκBα (GST-IκBα1–54; SEQ ID NO:3), but such phosphorylation cannot be detected in an IκBα derivative containing threonine substitutions at positions 32 and 36. In addition, IκB kinase activity is strongly inhibited by a doubly phosphorylated IκBα peptide (i.e., phosphorylated at S32 and S36), but not by an unrelated c-fos phosphopeptide that contains a single phosphothreonine. A further characteristic of an IKK signalsome is its ability to phosphorylate a substrate in vitro in a standard kinase buffer, without the addition of exogenous cofactors. Free ubiquitin is not detectable in preparations of IKK signalsome (see FIG. 10), even at very long exposures. Accordingly an IKK signalsome differs from the ubiquitin-dependent IκBα kinase activity described by Chen et al., *Cell* 84:853–62, 1996.

An IKK signalsome may be immunoprecipitated by antibodies raised against MKP-1 (MAP kinase phosphatase-1; Santa Cruz Biotechnology, Inc., Santa Cruz, Calif. #SC-1102), and its activity detected using an in vitro IκBα kinase assay. However, as discussed further below, MKP-1 does not appear to be a component of IκB kinase complex. The substrate specificity of the immunoprecipitated IKK signalsome is maintained (i.e., there is strong phosphorylation of wildtype GST-IκBα 1–54 (SEQ ID NO:3) and GST-IκBβ 1–44 (SEQ ID NO:4), and substantially no detectable phosphorylation of GST-IκBα 1–54 in which serines 32 and 36 are replaced by threonines (GST- IκBα S32/36 to T; SEQ ID NO:5) or GST-IκBβ 1–44 in which serines 19 and 23 are replaced by alanines (GST-IκBβ 1–44 S19/23 to A; SEQ ID NO:6)).

Figure 2:
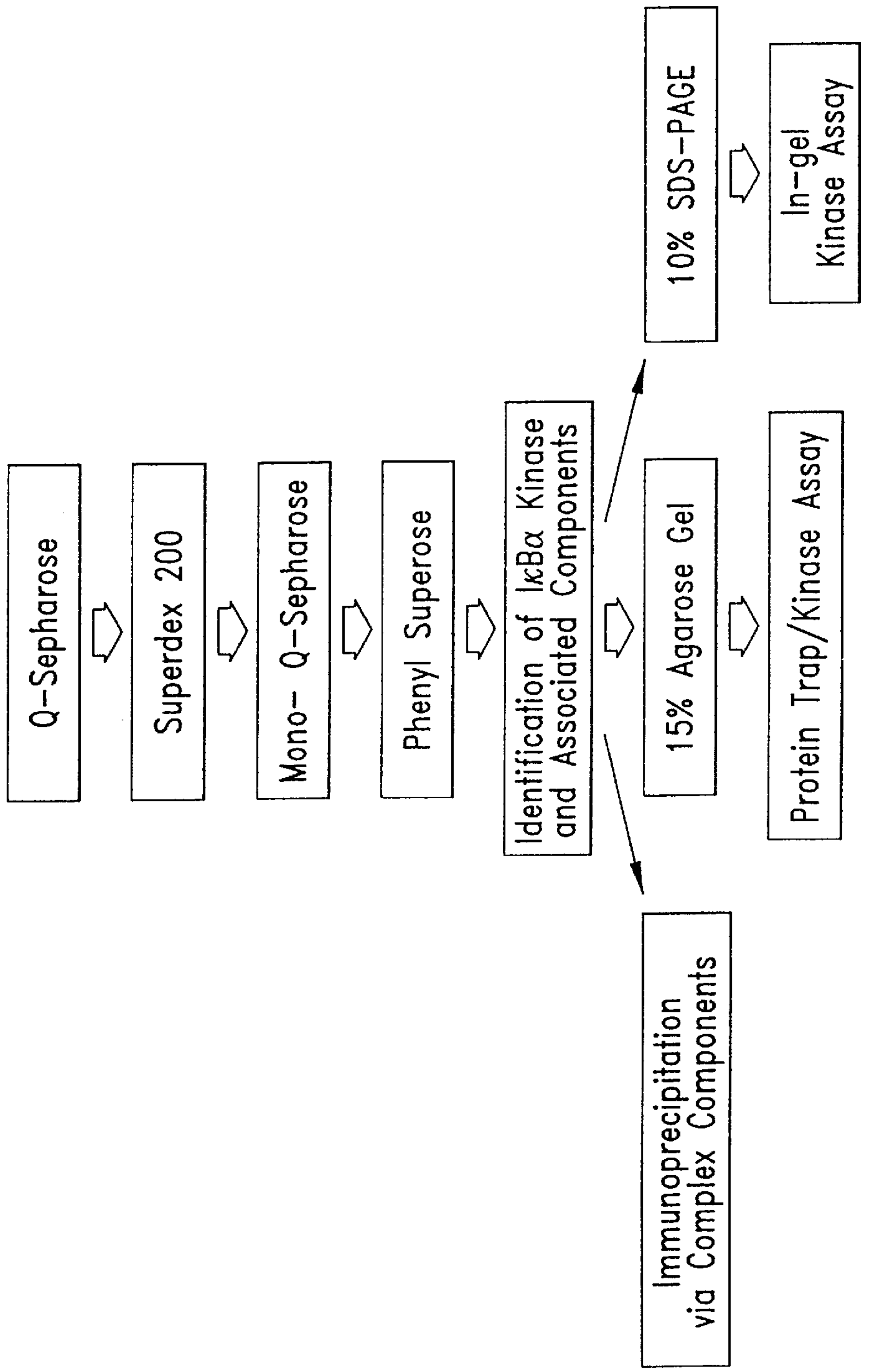
FIG. 2 is a flow chart depicting a representative purification procedure for the preparation of an IKK signalsome.

An IKK signalsome may be isolated from human or other cells, and from any of a variety of tissues and/or cell types. For example, using standard protocols, cytoplasmic and/or nuclear/membrane extracts may be prepared from HeLa S3 cells following seven minutes induction with 30 ng/mL TNFα. The extracts may then be subjected to a series of chromatographic steps that includes Q Sepharose, gel filtration (HiLoad 16/60 Superdex 200), Mono Q, Phenyl Superose, gel filtration (Superdex 200 10/30) and Mono Q. This representative purification procedure is illustrated in FIG. 2, and results in highly enriched IKK signalsome (compare, for example, FIGS. 5A and 6A).

Figure 11A:
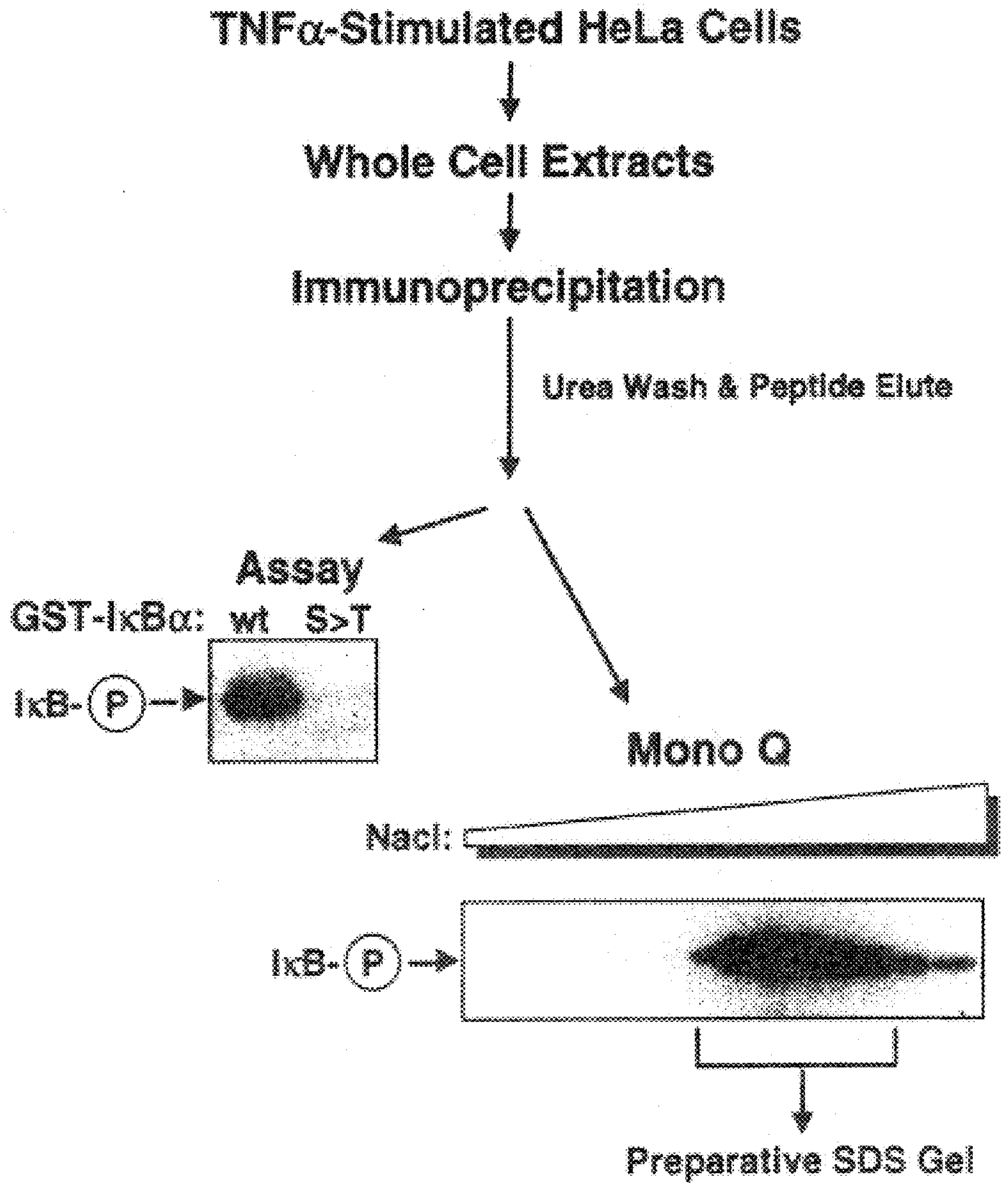
FIG. 11A illustrates a procedure for purification of the IKK signalsome. A whole cell extract was prepared from TNFα-stimulated (20 ng/ml, 7 minute induction) HeLa S3 cells (1.2 g total protein). The IKK signalsome was then immunoprecipitated from the extract using anti-MKP-1 antibodies, washed with buffer containing 3.5 M urea and eluted overnight at 4° C. in the presence of excess MKP-1 specific peptide. Eluted IKK signalsome was then fractionated on a Mono Q column, IκB kinase active fractions were pooled, concentrated and subjected to preparative SDS-PAGE. Individual protein bands were excised and submitted for peptide sequencing.

An alternative purification procedure employs a two-step affinity method, based on recognition of IKK signalsome by the MKP-1 antibody (FIG. 11A). Whole cell lysates from TNFα-stimulated HeLa cells may be immunoprecipitated with an anti-MKP-1 antibody. The IKK signalsome may be eluted with the specific MKP-1 peptide to which the antibody was generated and fractionated further on a Mono Q column.

Throughout the fractionation, an in vitro kinase assay may be used to monitor the IκB kinase activity of the IKK signalsome. In such an assay, the ability of a fraction to phosphorylate an appropriate substrate (such as IκBα (SEQ ID NO:1) or a derivative or variant thereof) is evaluated by any of a variety of means that will be apparent to those of ordinary skill in the art. For example, a substrate may be combined with a chromatographic fraction in a protein kinase buffer containing $^{32}P$ γ-ATP, phosphatase inhibitors and protease inhibitors. The mixture may be incubated for 30 minutes at 30° C. The reaction may then be stopped by the addition of SDS sample buffer and analyzed using SDS-PAGE with subsequent autoradiography. Suitable substrates include full length IκBα (SEQ ID NO:1), polypeptides comprising the N-terminal 54 amino acids of IκBα, full length IκBβ (SEQ ID NO:2) and polypeptides comprising the N-terminal 44 amino acids of IκBβ. Any of these substrates may be used with or without an N-terminal tag. One suitable substrate is a protein containing residues 1–54 of IκBα and an N-terminal GST tag (referred to herein as GST-IκBα 1–54; SEQ ID NO:3). To evaluate the specificity of an IκB kinase complex, IκBα mutants containing threonine or alanine residues at positions 32 and 36, and/or other modifications, may be employed.

Alternatively, an IKK signalsome may be prepared from its components which are also encompassed by the present invention. Such components may be produced using well known recombinant techniques, as described in greater detail below. Components of an IKK signalsome may be native, or may be variants of a native component (ie., a component sequence may differ from the native sequence in one or more substitutions and/or modifications, provided that the ability of a complex comprising the component variant to specifically phosphorylate IκBα is not substantially diminished). Substitutions and/or modifications may generally be made in non-critical and/or critical regions of the native protein. Variants may generally comprise residues of L-amino acids, D-amino acids, or any combination thereof. Amino acids may be naturally-occurring or may be non-natural, provided that at least one amino group and at least one carboxyl group are present in the molecule; α- and β-amino acids are generally preferred. A variant may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Component variants may also, or alternatively, contain other modifications, including the deletion or addition of amino acids that have minimal influence on the activity of the polypeptide. In particular, variants may contain additional amino acid sequences at the amino and/or carboxy termini. Such sequences may be used, for example, to facilitate purification or detection of the component polypeptide. In general, the effect of one or more substitutions and/or modifications may be evaluated using the representative assays provided herein.

A component may generally be prepared from a DNA sequence that encodes the component using well known recombinant methods. DNA sequences encoding components of an IKK signalsome may be isolated by, for example, screening a suitable expression library (i.e., a library prepared from a cell line or tissue that expresses IKK signalsome, such as spleen, leukocytes, HeLa cells or Jurkat cells) with antibodies raised against IKK signalsome or against one or more components thereof. Protein components may then be prepared by expression of the identified DNA sequences, using well known recombinant techniques.

Alternatively, partial sequences of the components may be obtained using standard biochemical purification and microsequencing techniques. For example, purified complex as described above may be run on an SDS-PAGE gel and individual bands may be isolated and subjected to protein microsequencing. DNA sequences encoding components may then be prepared by amplification from a suitable human cDNA library, using polymerase chain reaction (PCR) and methods well known to those of ordinary skill in the art. For example, an adapter-ligated cDNA library prepared from a cell line or tissue that expresses IKK signalsome (such as HeLa or Jurkat cells) may be screened using a degenerate 5' specific forward primer and an adapter-specific primer. Degenerate oligonucleotides may also be used to screen a cDNA library, using methods well known to those of ordinary skill in the art. In addition, known proteins may be identified via Western blot analysis using specific antibodies.

Components of an IKK signalsome may also be identified by performing any of a variety of protein-protein interaction assays known to those of ordinary skill in the art. For example, a known component can be used as "bait" in standard two-hybrid screens to identify other regulatory molecules, which may include IKK-1, IKK-2, NFκB1, RelA, IκBβ and/or p70 S6 kinase (Kieran et al., *Cell* 62:1007–1018, 1990; Nolan et al., *Cell* 64:961–69, 1991; Thompson et al., *Cell* 80:573–82, 1995; Grove et al., *Mol. Cell. Biol.* 11:5541–50, 1991).

Particularly preferred components of IKK signalsome are IκB kinases. An IκB kinase may be identified based upon its ability to phosphorylate one or more IκB proteins, which may be readily determined using the representative kinase assays described herein. In general, an IκB kinase is incorporated into an IKK signalsome, as described herein, prior to performing such assays, since an IκB kinase that is not complex-associated may not display the same phosphorylation activity as complex-associated IκB kinase. As noted above, an IκB kinase within an IKK signalsome specifically phosphorylates IκBα at residues S32 and S36, and phosphorylates IκBβ at residues 19 and 23, in response to specific stimuli.

As noted above, IKK-1 and IKK-2 are particularly preferred IκB kinases. IKK-1 and IKK-2 may be prepared by pooling the fractions from the Mono Q column containing peak IκB kinase activity and subjecting the pooled fractions to preparative SDS gel electrophoresis. The intensity of two prominent protein bands of ~85 and ~87 kDa (indicated by silver stain in FIG. 11B as IKK-1 and IKK-2 respectively) correlates with the profile of IκB kinase activity. The ~85 kDa band, corresponding to IKK-1, has been identified, within the context of the present invention, as CHUK (conserved helix-loop-helix ubiquitous kinase; see Connely and Marcu, *Cell. Mol. Biol. Res.* 41:537–49,1995). The ~87 kDa band contains IKK-2.

Figure 13B:
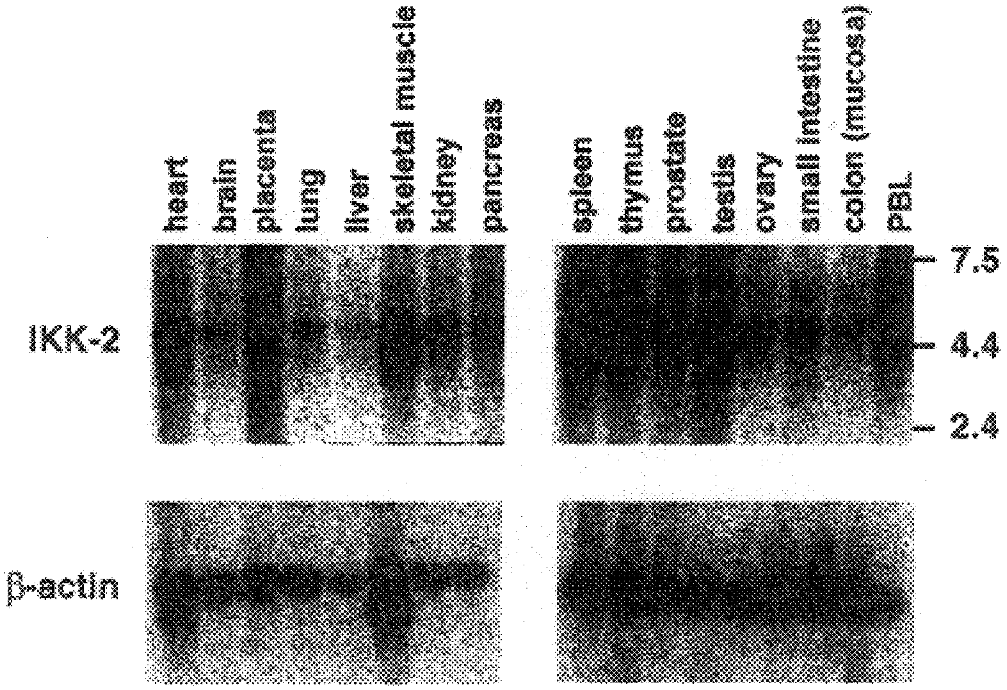
FIG. 13B is an autoradiogram depicting the results of Northern blot analysis of IKK-2 mRNA in adult human tissue. The source of the tissue is indicated at the top. Probes spanning the coding region of human IKK-2 and β-actin cDNA were used and are indicated to the left. Molecular weight standards are indicated to the right.

Sequence analysis reveals that IKK-1 and IKK-2 are related protein serine kinases (51% identity) containing protein interaction motifs (FIG. 13A). Both IKK-1 and IKK-2 contain the kinase domain at the N-terminus, and a leucine zipper motif and a helix-loop-helix motif in their C-terminal regions. Northern analysis indicates that mRNAs encoding IKK-2 are widely distributed in human tissues, with transcript sizes of ~4.5 kb and 6 kb (FIG. 13B). The sequences of IKK-1 and IKK-2 are also provided as SEQ ID NOs: 7 and 8, respectively.

Figure 14A:
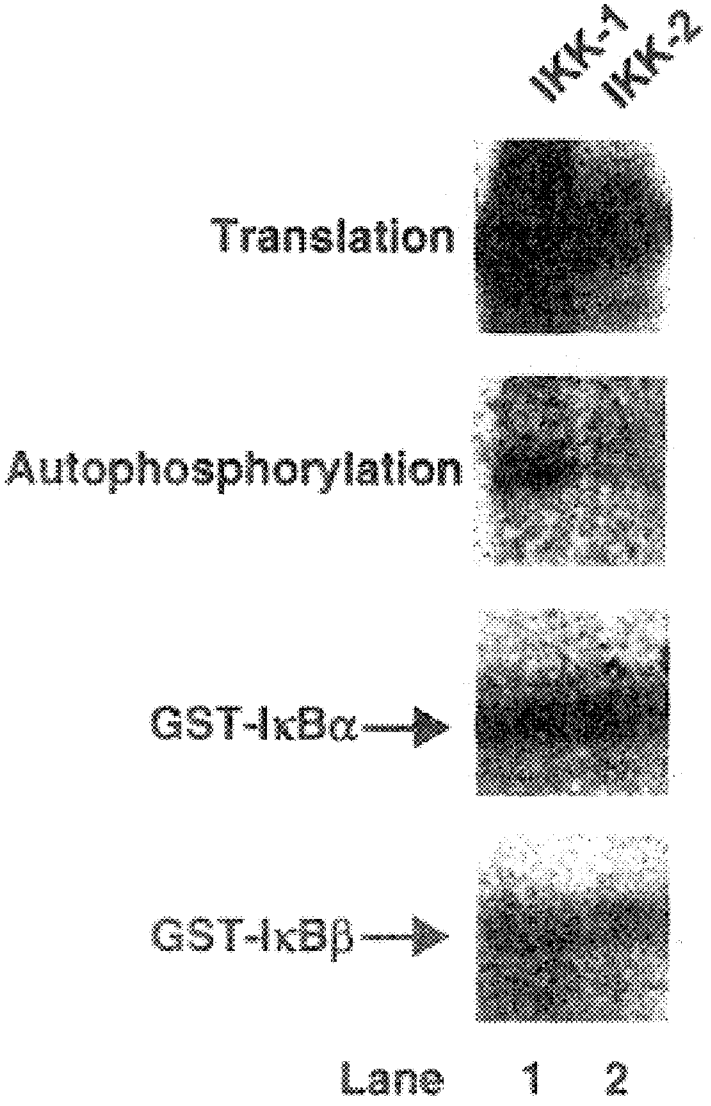
FIG. 14A is an autoradiogram depicting the results of kinase assays using IKK-1 and IKK-2. IKK-1 and IKK-2 were immunoprecipitated from rabbit reticulocyte lysates phosphorylate IκBα and IκBβ. Either HA-tagged IKK-1 (lane 1) or Flag-tagged IKK-2 (lane 2) were translated in rabbit reticulocyte lysates, immunoprecipitated, and examined for their ability to phosphorylate GST IκBα 1–54 WT and GST IκBβ 1–44 as indicated by an arrow to the left. IKK-1 (lane 1) undergoes significant autophosphorylation in contrast to IKK-2 (lane 2) which is identified only with longer exposure times.

It has been found, within the context of the present invention, that rabbit reticulocyte lysate immunoprecipitates that contain IKK-1 or IKK-2 phosphorylate IκBα and IκBβ with the correct substrate specificity (see FIG. 14A). Altered versions of these kinases interfere with translocation of RelA to the nucleus of TNFα-stimulated HeLa cells. Accordingly, IKK-1 and IKK-2 appear to control a significant early step of NFκB activation.

Other components of an IKK signalsome are also contemplated by the present invention. Such components may include, but are not limited to, upstream kinases such as MEKK-1 (Lee et al., *Cell* 88,:213–22, 1997; Hirano et al., *J. Biol. Chem.* 271:13234–38, 1996) or NIK (Malinin et al., *Nature* 385:540–44, 1997); adapter proteins that mediate an IKK-1:IKK-2 interaction; a component that crossreacts with anti-MKP-1; an inducible RelA kinase; and/or the E3 ubiquitin ligase that transfers multiubiquitin chains to phosphorylated IκB (Hershko and Ciechanover, *Annu. Rev. Biochem.* 61:761–807, 1992).

A component of an IKK signalsome may generally be prepared from DNA encoding the component by expression of the DNA in cultured host cells, which may be stable cell lines or transiently transfected cells. Preferably, the host cells are bacteria, yeast, baculovirus-infected insect cells or mammalian cells. The recombinant DNA may be cloned into any expression vector suitable for use within the host cell, using techniques well known to those of ordinary skill in the art. An expression vector may, but need not, include DNA encoding an epitope, such that the recombinant protein contains the epitope at the N- or C-terminus. Epitopes such as glutathione-S transferase protein (GST), HA (hemagglutinin)-tag, FLAG and Histidine-tag may be added using techniques well known to those of ordinary skill in the art.

The DNA sequences expressed in this manner may encode native components of an IKK signalsome, or may encode portions or variants of native components, as described above. DNA molecules encoding variants may generally be prepared using standard mutagenesis techniques, such as oligonucleotide-directed site-specific mutagenesis. Sections of the DNA sequence may also, or alternatively, be removed to permit preparation of truncated polypeptides and DNA encoding additional sequences such as "tags" may be added to the 5' or 3' end of the DNA molecule.

IKK signalsome components may generally be used to reconstitute IKK signalsome. Such reconstitution may be achieved in vitro by combining IKK signalsome components in a suitable buffer. Alternatively, reconstitution may be achieved in vivo by expressing components in a suitable host cell, such as HeLa or HUVEC, as described herein.

Expressed IKK signalsome, or a component thereof, may be isolated in substantially pure form. Preferably, IKK signalsome or a component is isolated to a purity of at least 80% by weight, more preferably to a purity of at least 95% by weight, and most preferably to a purity of at least 99% by weight. In general, such purification may be achieved using, for example, the representative purification methods described herein or the standard techniques of ammonium sulfate fractionation, SDS-PAGE electrophoresis, and affinity chromatography. IKK signalsome and components for use in the methods of the present invention may be native, purified or recombinant.

In one aspect of the present invention, an IKK signalsome and/or one or more components thereof may be used to identify modulating agents, which may be antibodies (e.g., monoclonal), polynucleotides or other drugs, that inhibit or stimulate signal transduction via the NF-κB cascade. Modulation includes the suppression or enhancement of NF-κB activity. Modulation may also include suppression or enhancement of IκB phosphorylation or the stimulation or inhibition of the ability of activated (i.e., phosphorylated) IKK signalsome to phosphorylate a substrate. Compositions that inhibit NF-κB activity by inhibiting IκB phosphorylation may include one or more agents that inhibit or block IκBα kinase activity, such as an antibody that neutralizes IKK signalsome, a competing peptide that represents the substrate binding domain of IκB kinase or a phosphorylation motif of IκB, an antisense polynucleotide or ribozyme that interferes with transcription and/or translation of IκB kinase, a molecule that inactivates IKK signalsome by binding to the complex, a molecule that binds to IκB and prevents phosphorylation by IKK signalsome or a molecule that prevents transfer of phosphate groups from the kinase to the substrate. Within certain embodiments, a modulating agent inhibits or enhances the expression or activity of IKK-1 and/or IKK-2.

In general, modulating agents may be identified by combining a test compound with an IKK signalsome, IκB kinase or a polynucleotide encoding an IκB kinase in vitro or in vivo, and evaluating the effect of the test compound on the IκB kinase activity using, for example, a representative assay described herein. An increase or decrease in kinase activity can be measured by adding a radioactive compound, such as $^{32}$P-ATP and observing radioactive incorporation into a suitable substrate for IKK signalsome, thereby determining whether the compound inhibits or stimulates kinase activity. Briefly, a candidate agent may be included in a reaction mixture containing compounds necessary for the kinase reaction (as described herein) and IκB substrate, along with IKK signalsome, IκB kinase or a polynucleotide encoding an IκB kinase. In general, a suitable amount of antibody or other agent for use in such an assay ranges from about 0.01 μM to about 10 μM. The effect of the agent on IκB kinase activity may then be evaluated by quantitating the incorporation of [$^{32}$P]phosphate into an IκB such as IκBα (or a derivative or variant thereof), and comparing the level of incorporation with that achieved using IκB kinase without the addition of a candidate agent. Alternatively, the effect of a candidate modulating agent on transcription of an IκB kinase may be measured, for example, by Northern blot analysis or a promoter/reporter-based whole cell assay.

Alternatively, for assays in which the test compound is combined with an IKK signalsome, the effect on a different IKK signalsome activity may be assayed. For example, an IKK signalsome also displays p65 kinase activity and IKK phosphatase activity. Assays to evaluate the effect of a test compound on such activities may be performed using well known techniques. For example, assays for p65 kinase activity may generally be performed as described by Zhong et al., *Cell* 89:413–24, 1997. For phosphatase activity, an assay may generally be performed as described by Sullivan et al., *J. Biomolecular Screening* 2:19–24, 1997, using a recombinant phosphorylated IκB kinase as a substrate.

In another aspect of the present invention, IKK signalsome or IκB kinase may be used for phosphorylating an IκB such as IκBα (or a derivative or variant thereof) so as to render it a target for ubiquitination and subsequent degradation. IκB may be phosphorylated in vitro by incubating IKK signalsome or IκB kinase with IκB in a suitable buffer for 30 minutes at 30° C. In general, about 0.01 μg to about 9 μg of IκB kinase complex is sufficient to phosphorylate from about 0.5 μg to about 2 μg of IκB. Phosphorylated substrate may then be purified by binding to GSH-sepharose and washing. The extent of substrate phosphorylation may generally be monitored by adding [γ-$^{32}$P]ATP to a test aliquot, and evaluating the level of substrate phosphorylation as described herein.

An IKK signalsome, component thereof, modulating agent and/or polynucleotide encoding a component and/or modulating agent may also be used to modulate NF-κB activity in a patient. Such modulation may occur by any of a variety of mechanisms including, but not limited to, direct inhibition or enhancement of IκB phosphorylation using a component or modulating agent; or inhibiting upstream activators, such as NIK or MEK, with IKK signalsome or a component thereof. As used herein, a "patient" may be any mammal, including a human, and may be afflicted with a disease associated with IκB kinase activation and the NF-κB cascade, or may be free of detectable disease. Accordingly, the treatment may be of an existing disease or may be prophylactic. Diseases associated with the NF-κB cascade include inflammatory diseases, neurodegenerative diseases, autoimmune diseases, cancer and viral infection.

Treatment may include administration of an IKK signalsome, a component thereof and/or an agent which modulates IκB kinase activity. For administration to a patient, one or more such compounds are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Any suitable carrier known to those of ordinary skill in the art may be employed in the pharmaceutical compositions of the present invention. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

Alternatively, a pharmaceutical composition may comprise a polynucleotide encoding a component of an IKK signalsome and/or a modulating agent (such that the component and/or modulating agent is generated in situ) in combination with a physiologically acceptable carrier. In such pharmaceutical compositions, the polynucleotide may be present within any of a variety of delivery systems known to those of ordinary skill in the art, including nucleic acid, bacterial and viral expression systems, as well as colloidal dispersion systems, including liposomes. Appropriate nucleic acid expression systems contain the necessary polynucleotide sequences for expression in the patient (such as a suitable promoter and terminating signal). DNA may also be "naked," as described, for example, in Ulmer et al., *Science* 259:1745–49, 1993.

Various viral vectors that can be used to introduce a nucleic acid sequence into the targeted patient's cells include, but are not limited to, vaccinia or other pox virus, herpes virus, retrovirus, or adenovirus. Techniques for incorporating DNA into such vectors are well known to those of ordinary skill in the art. Preferably, the retroviral vector is a derivative of a murine or avian retrovirus including, but not limited to, Moloney murine leukemia virus (MoMuLV), Harvey murine sarcoma virus (HaMuSV), murine mammary tumor virus (MuMTV), and Rous Sarcoma Virus (RSV). A retroviral vector may additionally transfer or incorporate a gene for a selectable marker (to aid in the identification or selection of transduced cells) and/or a gene that encodes the ligand for a receptor on a specific target cell (to render the vector target specific). For example, retroviral vectors can be made target specific by inserting a nucleotide sequence encoding a sugar, a glycolipid, or a protein. Targeting may also be accomplished using an antibody, by methods known to those of ordinary skill in the art.

Viral vectors are typically non-pathogenic (defective), replication competent viruses, which require assistance in order to produce infectious vector particles. This assistance can be provided, for example, by using helper cell lines that contain plasmids that encode all of the structural genes of the retrovirus under the control of regulatory sequences within the LTR, but that are missing a nucleotide sequence which enables the packaging mechanism to recognize an RNA transcript for encapsulation. Such helper cell lines include (but are not limited to) Ψ2, PA317 and PA12. A retroviral vector introduced into such cells can be packaged and vector virion produced. The vector virions produced by this method can then be used to infect a tissue cell line, such as NIH 3T3 cells, to produce large quantities of chimeric retroviral virions.

Another targeted delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques* 6:882, 1988).

The targeting of liposomes can be classified based on anatomical and mechanistic factors. Anatomical classification is based on the level of selectivity and may be, for example, organ-specific, cell-specific, and/or organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

Routes and frequency of administration, as well doses, will vary from patient to patient. In general, the pharmaceutical compositions may be administered intravenously, intraperitoneally, intramuscularly, subcutaneously, intracavity or transdermally. Between 1 and 6 doses may be administered daily. A suitable dose is an amount that is sufficient to show improvement in the symptoms of a patient afflicted with a disease associated with the NF-κB cascade. Such improvement may be detected by monitoring inflammatory responses (e.g., edema, transplant rejection, hypersensitivity) or through an improvement in clinical symptoms associated with the disease. The dosage may generally vary depending on the nature of the modulating agent and the disease to be treated. Typically, the amount of modulating agent present in a dose, or produced in situ by DNA present in a dose, ranges from about 1 μg to about 200 mg per kg of host. Suitable dose sizes will vary with the size of the patient, but will typically range from about 10 mL to about 500 mL for 10–60 kg animal.

In another aspect, the present invention provides methods for detecting the level of stimulus-inducible IκB kinase activity in a sample. The level of IκB kinase activity may generally be determined via an immunokinase assay, in which IKK signalsome is first immunoprecipitated with an antibody that binds to the complex. The immunoprecipitated material is then subjected to a kinase assay as described herein. Substrate specificity may be further evaluated as described herein to distinguish the activity of a stimulus-inducible IκB kinase complex from other kinase activities.

The present invention also provides methods for detecting the level of IKK signalsome, or a component thereof, in a sample. The amount of IKK signalsome, IκB kinase or nucleic acid encoding IκB kinase, may generally be determined using a reagent that binds to IκB kinase, or to DNA or RNA encoding a component thereof. To detect nucleic acid encoding a component, standard hybridization and/or PCR techniques may be employed using a nucleic acid probe or a PCR primer. Suitable probes and primers may be designed by those of ordinary skill in the art based on the component sequence. To detect IKK signalsome or a component thereof, the reagent is typically an antibody, which may be prepared as described below.

There are a variety of assay formats known to those of ordinary skill in the art for using an antibody to detect a protein in a sample. See, e.g., Harlow and Lane, *Antibodies: A Laboratory Manual,* Cold Spring Harbor Laboratory, 1988. For example, the antibody may be immobilized on a solid support such that it can bind to and remove the protein from the sample. The bound protein may then be detected using a second antibody that binds to the antibody/protein complex and contains a detectable reporter group. Alternatively, a competitive assay may be utilized, in which protein that binds to the immobilized antibody is labeled with a reporter group and allowed to bind to the immobilized antibody after incubation of the antibody with the sample. The extent to which components of the sample inhibit the binding of the labeled protein to the antibody is indicative of the level of protein within the sample. Suitable reporter groups for use in these methods include, but are not limited to, enzymes (e.g., horseradish peroxidase), substrates, cofactors, inhibitors, dyes, radionuclides, luminescent groups, fluorescent groups and biotin.

Antibodies encompassed by the present invention may be polyclonal or monoclonal, and may bind to IKK signalsome and/or one or more components thereof (e.g., IKK-1 and/or IKK-2). Preferred antibodies are those antibodies that inhibit or block IκB kinase activity in vivo and within an in vitro assay, as described above. Other preferred antibodies are those that bind to one or more IκB proteins. As noted above, antibodies and other agents having a desired effect on IκB kinase activity may be administered to a patient (either prophylactically or for treatment of an existing disease) to modulate the phosphorylation of an IκB, such as IκBα, in vivo.

Antibodies may be prepared by any of a variety of techniques known to those of ordinary skill in the art (see, e.g., Harlow and Lane, *Antibodies: A Laboratory Manual,* Cold Spring Harbor Laboratory, 1988). In one such technique, an immunogen comprising the protein of interest is initially injected into a suitable animal (e.g, mice, rats, rabbits, sheep and goats), preferably according to a predetermined schedule incorporating one or more booster immunizations, and the animals are bled periodically. Polyclonal antibodies specific for the protein may then be purified from such antisera by, for example, affinity chromatography using the protein coupled to a suitable solid support.

Monoclonal antibodies specific for an IKK signalsome or a component thereof may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the complex and/or component of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

In a related aspect of the present invention, kits for detecting the level of IKK signalsome, IκB kinase, nucleic acid encoding IκB kinase and/or IκB kinase activity in a sample are provided. Any of a variety of samples may be used in such assays, including eukaryotic cells, bacteria, viruses, extracts prepared from such organisms and fluids found within living organisms. In general, the kits of the present invention comprise one or more containers enclosing elements, such as reagents or buffers, to be used in the assay.

A kit for detecting the level of IKK signalsome, IκB kinase or nucleic acid encoding IκB kinase typically contains a reagent that binds to the compound of interest. To detect nucleic acid encoding IκB kinase, the reagent may be a nucleic acid probe or a PCR primer. To detect IKK signalsome or IκB kinase, the reagent is typically an antibody. Such kits also contain a reporter group suitable for direct or indirect detection of the reagent (i.e., the reporter group may be covalently bound to the reagent or may be bound to a second molecule, such as Protein A, Protein G, immunoglobulin or lectin, which is itself capable of binding to the reagent). Suitable reporter groups include, but are not limited to, enzymes (e.g., horseradish peroxidase), substrates, cofactors, inhibitors, dyes, radionuclides, luminescent groups, fluorescent groups and biotin. Such reporter groups may be used to directly or indirectly detect binding of the reagent to a sample component using standard methods known to those of ordinary skill in the art.

In yet another aspect, IKK signalsome may be used to identify one or more native upstream kinases (i.e., kinases that phosphorylate and activate IKK signalsome in vivo) or other regulatory molecules that affect IκB kinase activity (such as phosphatases or molecules involved in ubiquitination), using methods well known to those of ordinary skill in the art. For example, IKK signalsome components may be used in a yeast two-hybrid system to identify proteins that interact with such components. Alternatively, an expression library may be screened for cDNAs that phosphorylate IKK signalsome or a component thereof.

The following Examples are offered by way of illustration and not by way of limitation.

EXAMPLES

Example 1

Recruitment of NFκB into IKK Signalsome During Activation

This example illustrates the recruitment of NFκB into a protein complex (the IKK signalsome) containing IκB kinase and other signaling proteins.

Cytoplasmic extracts of either unstimulated or stimulated Jurkat cells were fractionated on a Superdex 200 gel filtration column, and IκBα was visualized by immunoblot analysis. Jurkat cells were grown to a cell density of $1.5\times10^6$ cells/ml and either not stimulated or induced for 10 minutes with PMA (50 ng/ml)/PHA (1 μg/ml). Cells were harvested and resuspended in two volumes HLB buffer (20 mM Tris pH 8.0, 2 mM EDTA, 1 mM EGTA, 10 mM β-glycerophosphate, 10 mM NaF, 10 mM PNPP, 300 μM $Na_3VO_4$, 1 mM benzamidine, 2 mM PMSF, 10 μg/ml aprotonin, 1 μg/ml leupeptin, 1 μg/ml pepstatin, 1 mM DTT), made 0.1% NP40 and left on ice for 15 minutes, and lysed with a glass Dounce homogenizer. The nuclei were pelleted at 10,000 rpm for 20 minutes in a Sorval SS34 rotor. The supernatant was further centrifuged at 40,000 rpm for 60 min in a Ti50.1 rotor. All procedures were carried out at 4° C. The S-100 fraction was concentrated and chromatographed on Hi Load 16/60 Superdex 200 prep grade gel filtration column that was equilibrated in GF buffer (20 mM Tris HCl pH 8.0, 150 mM NaCl, 1 mM EDTA, 1 mM EGTA, 5% glycerol, 0.025% Brij 35, 1 mM benzamidine, 2 mM PMSF, 10 mM β-glycerophosphate, 10 mM NaF, 10 mM PNPP, 300 μM $Na_3VO_4$, 10 μg/ml aprotonin, 1 μg/ml leupeptin, 1 μg/ml pepstatin, 1 mM DTT). Isolated fractions were analyzed by western blot analysis using either anti-IκBα or anti-JNK antibodies (Santa Cruz, Inc., Santa Cruz, Calif.).

Figure 1A:
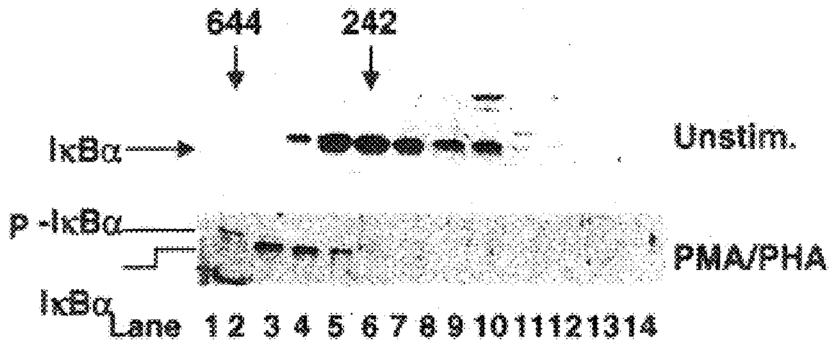
FIGS. 1A–1C are autoradiograms depicting the results of immunoblot analyses.

As shown in FIG. 1A, IκBα in cell extracts from unstimulated cells eluted with an apparent molecular weight of ~300 kDa (lanes 5–7), consistent with the chromatographic properties of the inactive NFκB-IκB complex (Baeuerle and Baltimore, *Genes Dev.* 3:1689–98, 1989). In contrast, phosphorylated IκBα (from cells stimulated for periods too short to permit complete degradation of the protein) migrated at ~600 kDa on the same chromatography columns (lanes 2, 3). This difference in migration was specific for IκB, since analysis of the same fractions indicated that the Jun N-terminal kinases JNK1 and JNK2 migrated with low apparent molecular weight and showed no difference in chromatographic behavior between stimulated and unstimulated cells. Stimulation-dependent recruitment of IκB into this larger protein complex corresponded with the appearance of phosphorylated IκB, suggesting that the complex contained the specific IκB kinases that mediate IκB phosphorylation. These results demonstrate that that NFκB activation involves recruitment into a protein complex (the IKK signalsome) containing IκB kinase and other signaling proteins.

Example 2

Partial Purification of IKK Signalsome and Identification of Co-purifying Components This Example illustrates the fractionation of extracts containing IκB kinase. Whole cell extracts from TNFα-stimulated cells were fractionated by gel filtration, ion exchange, and other chromatographic methods, as described above. IκB kinase activity in the fractions was assayed by phosphorylation of GST-IκBα (1–54) (SEQ ID NO:3) or GST-IκBβ (1–44) (SEQ ID NO:4). Kinase assays were performed in 20 mM HEPES pH 7.7, 2 mM $MgCl_2$, 2 mM $MnCl_2$, 10 μM ATP, 1–3 μCi γ-[$^{32}$P]-ATP, 10 mM β-glycerophosphate, 10 mM NaF, 10 mM PNPP, 300 μM $Na_3VO_4$, 1 mM benzamidine, 2 μM PMSF, 10 μg/ml aprotonin, 1 μg/ml leupeptin, 1 μg/ml pepstatin, 1 mM DTT) at 30° C. for 30 to 60 minutes in the presence of the indicated substrate. The kinase reaction was stopped by the addition of 6×SDS-PAGE sample buffer, subjected to SDS-PAGE analysis and visualized using autoradiography. GST-IκB substrates for use in the above assay were prepared using standard techniques for bacterially expressed GST-protein (see *Current Protocols in Molecular Biology* 2:16.7.1–16.7.7, 1996). Bacterial cells were lysed, GST proteins were purified via binding to GST-agarose beads, washed several times, eluted from the beads with glutathione, dialyzed against kinase assay buffer and stored at −80° C. The specificity of the kinase was established by using mutant GST-IκBα (1–54) in which serines 32, 36 had been mutated to threonine (SEQ ID NO:5), and GST-IκBβ (1–44) in which serines 19, 23 had been mutated to alanine (SEQ ID NO:6).

Figure 1B:
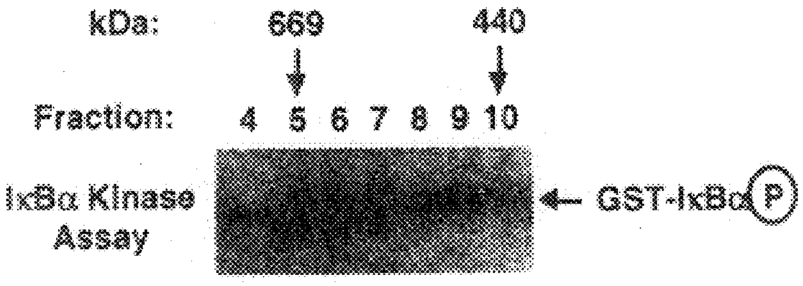

IκB kinase activity was not observed in extracts from unstimulated cells, while stimulation with TNFα for 5–7 minutes resulted in strong induction of kinase activity. As shown in FIG. 1B, the IκB kinase activity from stimulated cells chromatographed on gel filtration as a broad peak of ~500–700 kDa, consistent with its presence in a large protein complex potentially containing other components required for NFκB activation.

Figure 1C:
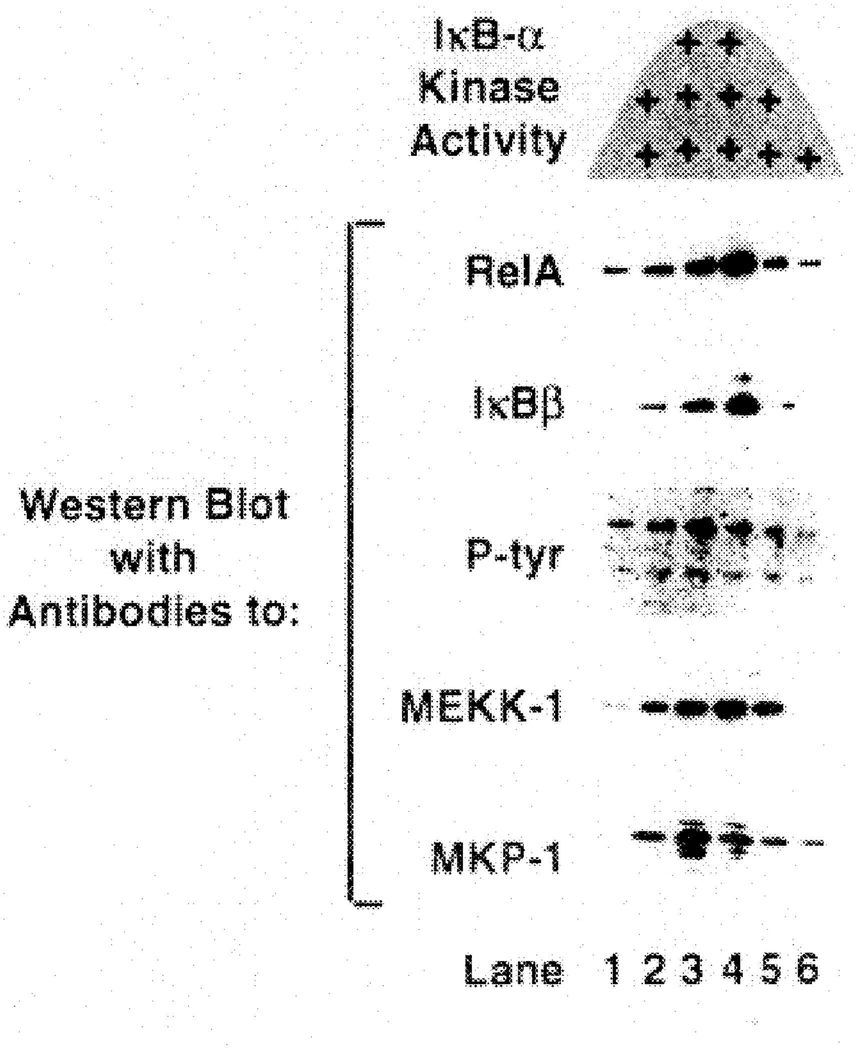

NFκB activation is known to occur under conditions that also stimulate MAP kinase pathways (Lee et al., *Cell* 88:213–22, 1997; Hirano, et al., *J. Biol. Chem.* 271:13234–38, 1996). Accordingly, further experiments were performed to detect proteins associated with MAP kinase and phosphatase cascades at various stages of purification of the IKK signalsome. In addition to RelA and IκBβ, MEKK-1 and two tyrosine-phosphorylated proteins of ~55 and ~40 kDa copurified with IκB kinase activity (FIG. 1C). Antibodies to Rel A and IκBβ were obtained from Santa Cruz Biotechnology, Inc. (Santa Cruz, Calif.), and antibodies to MEKK-1 were obtained from Upstate Biotechnology (Lake Placid, N.Y.). Other signaling components, including PKCζ, PP1 and PP2A, were detected in the same fractions as the IκB kinase in early chromatographic steps but did not copurify at later chromatographic steps (data not shown). Most interestingly, an unidentified protein of ~50 kDa, detected by its crossreaction with an antibody to MKP-1, copurified with IκB kinase through several purification steps (FIG. 1C). This protein is unlikely to be MKP-1 itself, since the molecular weight of authentic MKP-1 is 38 kDa.

Example 3

Preparation of IKK Signalsome from HeLa S3 Cell Extracts

This Example illustrates an alternate preparation of an IKK signalsome, and the characterization of the complex.

HeLa S3 cells were grown to a cell density of approximately $0.6\times10^6$/mL, concentrated 10 fold and induced with TNFα (30 ng/mL) for seven minutes. Two volumes of ice-cold PBS containing phosphatase inhibitors (10 mM sodium fluoride, 0.3 mM sodium orthovanadate and 20 mM β-glycerophosphate) were then added. The cells were spun down, washed once with ice-cold PBS containing phosphatase inhibitors and snap frozen.

Standard protocols were then used to prepare cytoplasmic and nuclear extracts. More specifically, the frozen HeLa S3 cell pellet was quick-thawed at 37° C., resuspended in 2 volumes of ice-cold Hypotonic Lysis Buffer (20 mM Tris pH 8.0, 2 mM EDTA, 1 mM EGTA, 10 mM β-glycerophosphate, 10 mM NaF, 10 mM PNPP, 0.3 mM $Na_2VO_4$, 5 mM sodium pyrophosphate, 1 mM benzamidine, 2 mM PMSF, 10 μg/mL aprotinin, 1 μg/mL leupeptin and 1 kg/mL pepstatin), and left to incubate on ice for 30 min. The swollen cells were then dounced 30 times using a tight pestle and the nuclei were pelleted at 10,000 rpm for 15 minutes at 4° C. The supernatant was clarified via ultracentrifugation (50,000 rpm for 1 hour at 4° C.) to generate the final cytoplasmic extract. The nuclear/membrane pellet was resuspended in an equal volume of High Salt Extraction Buffer (20 mM Tris pH 8.0, 0.5M NaCl, 1 mM EDTA, 1 mM EGTA, 0.25% Triton X-100, 20 mM β-glycerophosphate, 10 mM NaF, 10 mM PNPP, 0.3 mM $Na_2VO_4$, 1 mM benzamidine, 1 mM PMSF, 1 mM DTT, 10 μg/mL aprotinin, 1 μg/mL leupeptin and 1 μg/mL pepstatin) and allowed to rotate at 4° C. for 30 minutes. Cell debris was removed via centrifugation at 12,500 rpm for 30 minutes at 4° C. and the resulting supernatant was saved as the nuclear/membrane extract.

These extracts were then independently subjected to a series of chromatographic steps (shown in FIG. 2) using a Pharmacia FPLC system (Pharmacia Biotech, Piscataway, N.J.):

(1) Q Sepharose (Pharmacia Biotech, Piscataway, N.J.)—the column was run with a linear gradient starting with 0.0M NaCl Q Buffer (20 mM Tris pH 8.0, 0.5 mM EDTA, 0.5 mM EGTA, 0.025% Brij 35, 20 mM β-glycerophosphate, 10 mM NaF, 0.3 mM $Na_2VO_4$, 1 mM benzamidine, 1 mM PMSF, 2 mM DTT, 10 μg/mL aprotinin, 1 μg/mL leupeptin and 1 μg/mL pepstatin) and ending with 0.5M NaCl Q Buffer. The IκBα kinase activity eluted between 0.25 and 0.4 M NaCl.

(2) Gel Filtration HiLoad 16/60 Superdex 200) (Pharmacia Biotech, Piscataway, N.J.)—the column was run with Gel Filtration Buffer (20 mM Tris pH 8.0, 150 mM NaCl, 1 mM EDTA, 1 mM EGTA, 0.05% Brij 35, 20 mM β-glycerophosphate, 10 mM NaF, 0.3 mM $Na_2VO_4$, 1 mM benzamidine, 1 mM PMSF, 1 mM DTT, 10 μg/mL aprotinin, 1 μg/mL leupeptin and 1 μg/mL pepstatin). The peak IκBα kinase activity eluted at 40–48 mL, which corresponds to a molecular weight of 731 kD to 623 kD.

(3) HR 5/5 Mono Q (Pharmacia Biotech, Piscataway, N.J.)—the column was run with a linear gradient starting with 0.0M NaCl Q Buffer and ending with 0.5M NaCl Q Buffer (without Brij detergent to prepare sample for Phenyl Superose column). The IκBα kinase activity eluted between 0.25 and 0.4 M NaCl.

(4) HR Phenyl Superose (Pharmacia Biotech, Piscataway, N.J.)—the column was run with a linear gradient of 1.0M to 0.0M ammonium sulfate in Phenyl Superose Buffer (20 mM Tris pH 8.0, 0.25 mM EDTA, 1 mM EGTA, 20 mM β-glycerophosphate, 10 mM NaF, 0.1 mM $Na_2VO_4$, 1 mM benzamidine, 1 mM PMSF, 1 mM DTT, 10 μg/mL aprotinin, 1 μg/mL leupeptin and 1 μg/mL pepstatin). The IκBα kinase activity eluted between 0.35 and 0.2 M ammonium sulfate.

(5) Gel Filtration Superdex 200 HR 10/30 (Pharmacia Biotech, Piscataway, N.J.)—the column was run with Gel Filtration Buffer (see (2), above). The peak of activity eluted at 8–10 mL, which corresponds to a molecular weight of 720 kD to 600 kD.

(6) HR 5/5 Mono Q—the column was run as in (3) above except that the 0.05% Brij 35 was included in all Q buffers.

IκBα kinase activity, with similar substrate specificity and molecular weight, was isolated from both the cytoplasmic and nuclear/membrane extracts.

At each step of the fractionation, IκB kinase activity was monitored using an in vitro assay. The assay was performed by combining 2 μg of the respective IκB substrate (GST-IκBα 1–54 (wildtype) or GST-IκBα (S32/36 to T), as described below) with 3–5 μL chromatographic fraction and 20 μL of Kinase Assay Buffer (20 mM HEPES pH 7.4, 10 mM $MgCl_2$, 10 mM $MnCl_2$, 20 mM NaCl, 1 mM DTT, 20 mM PNPP, 20 μM ATP, 20 mM β-glycerophosphate, 10 mM NaF, 0.1 mM $Na_2VO_4$, 1 mM benzamidine, 1 mM PMSF) containing $\gamma^{32}$P-ATP, and incubating for 30 minutes at 30° C. The kinase reaction was terminated by adding 8 μL of 6×SDS-PAGE sample buffer. The entire sample was run on a 12% polyacrylamide gel, dried and subjected to autoradiography.

IκB substrates for use in the above assay were prepared using standard techniques (see Haskill et al., *Cell* 65:1281–1289, 1991). The GST-IκBα 1–54 (wildtype) or GST-IκBα (S32/36 to T) substrates were prepared using standard techniques for bacterially expressed GST-protein. Bacterial cells were lysed, GST proteins were purified via binding to GST-agarose beads, washed several times, eluted from the beads with glutathione, dialyzed against 50 mM NaCl Kinase Assay Buffer and stored at −80° C.

The TNFα-inducibility of IκB kinase activity was initially evaluated by Western blot analysis of the levels of IκB in HeLa S3 cytoplasmic extracts following gel filtration. IκBα was assayed by running 18 μL of the gel filtration fractions on 10% SDS PAGE, transferring to Nitrocellulose Membrane (Hybond-ECL, Amersham Life Sciences, Arlington Height, Ill.) using standard blotting techniques and probing with anti-IκBα antibodies (Santa Cruz Biotechnology, Inc., Santa Cruz, Calif.). TNFα-inducibility was evaluated by comparing the level of IκBα in cells that were (FIG. 3B) and were not (FIG. 3A) exposed to TNFα (30 ng/mL for seven minutes, as described above).

Figure 4A:
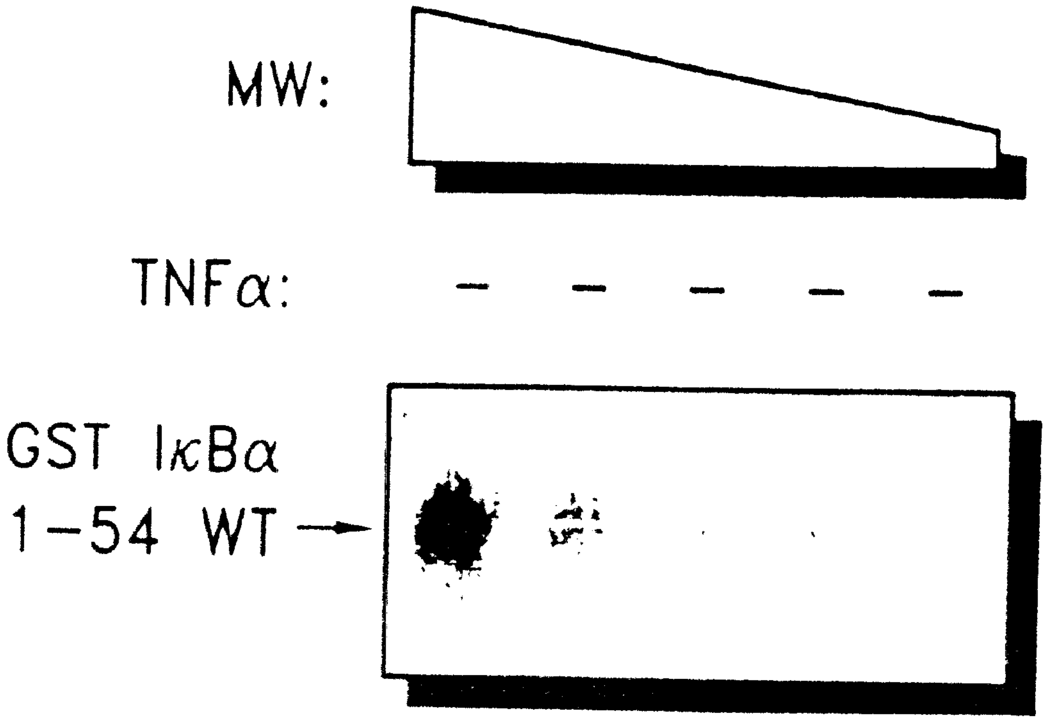
FIGS. 4A and 4B are autoradiograms depicting the results of an in vitro kinase assay in which the ability of the above cell extracts to phosphorylate the N-terminal portion of IκBα was evaluated.
Figure 4B:
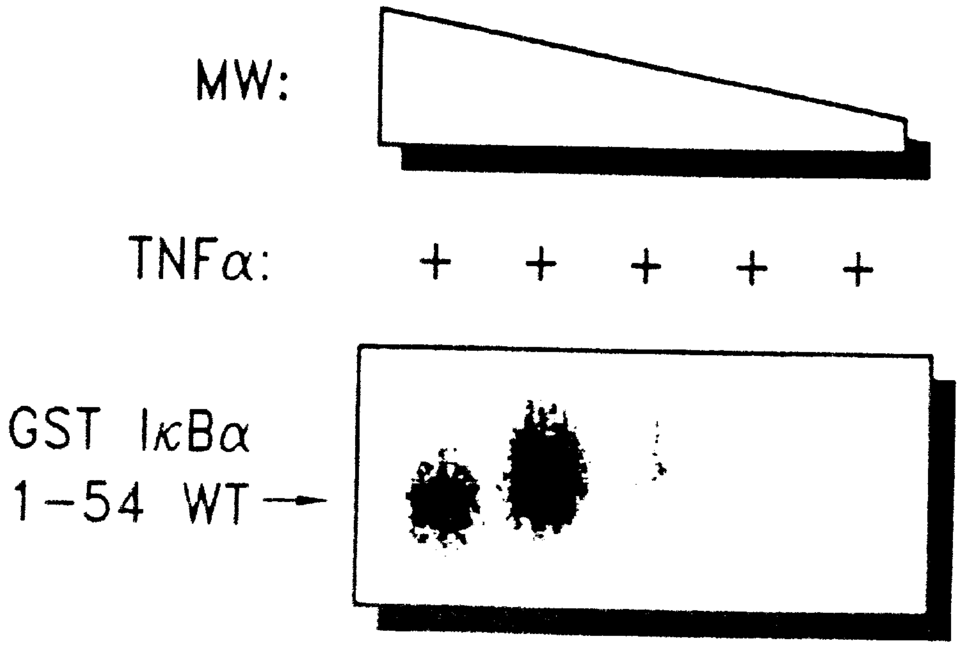

The IκB kinase activity of these cytoplasmic extracts was evaluated using the kinase assay described above. As shown in FIG. 4B, the extract of TNFα-treated cells phosphorylated GST-IκBα 1–54 (wildtype), while the untreated cell extract showed significantly lower levels of IκBα kinase activity (FIG. 4A).

Figure 5A:
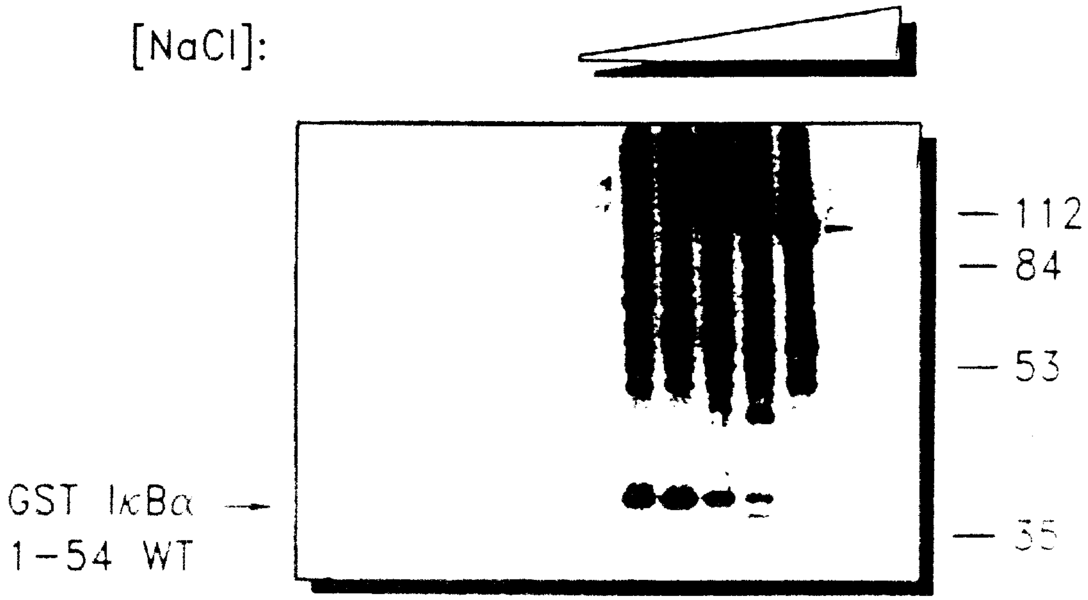
FIGS. 5A and 5B are autoradiograms depicting the results of an in vitro kinase assay using a cytoplasmic extract of TNFα-treated HeLa S3 cells, where the extract is subjected to Q Sepharose fractionation. The substrate was the truncated IκBα (residues 1 to 54), with FIG. 5A showing the results obtained with the wild type IκBα sequence and FIG. 5B presenting the results obtained using a polypeptide containing threonine substitutions at positions 32 and 36.
Figure 5B:
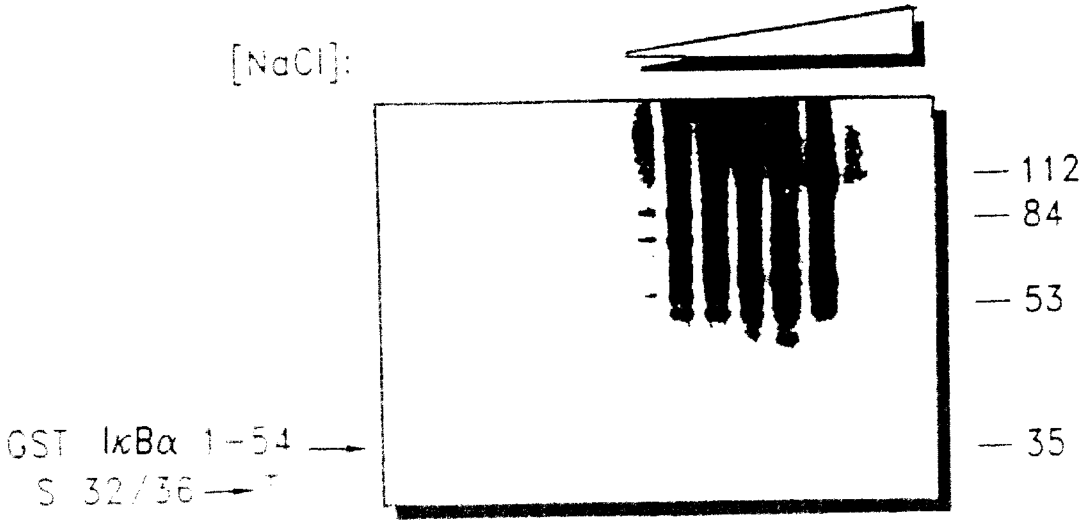

Cytoplasmic extracts of TNFα-treated HeLa S3 cells (following Q Sepharose fractionation) were also subjected to in vitro kinase assays, using the N-terminal portion of IκBα (residues 1 to 54) as substrate. With the wild type substrate, phosphorylation of GST-IκBα 1–54 was readily apparent (FIG. 5A). In contrast, substrate containing threonine substitutions at positions 32 and 36 was not phosphorylated (FIG. 5B).

Figure 6A:
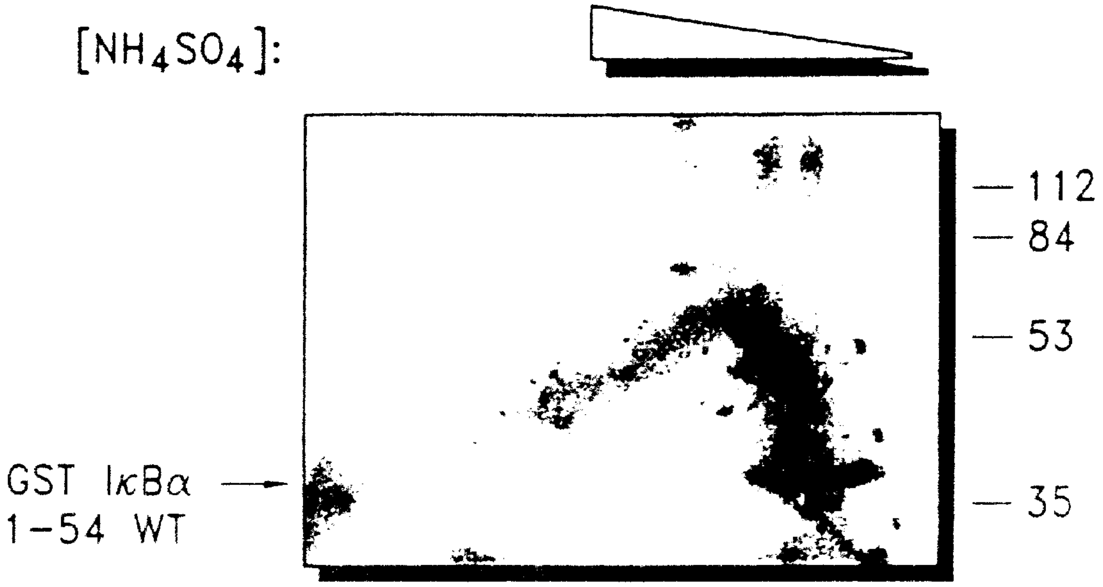
FIGS. 6A and 6B are autoradiograms depicting the results of an in vitro kinase assay using a cytoplasmic extract of TNFα-treated HeLa S3 cells, where the extract was subjected in series to chromatographic fractionation by Q Sepharose, Superdex 200, Mono Q Sepharose and Phenyl Superose. The substrate was the truncated IκBα (residues 1 to 54), with FIG. 6A showing the results obtained with the wild type IκBα sequence and FIG. 6B presenting the results obtained using a polypeptide containing threonine substitutions at positions 32 and 36.
Figure 6B:
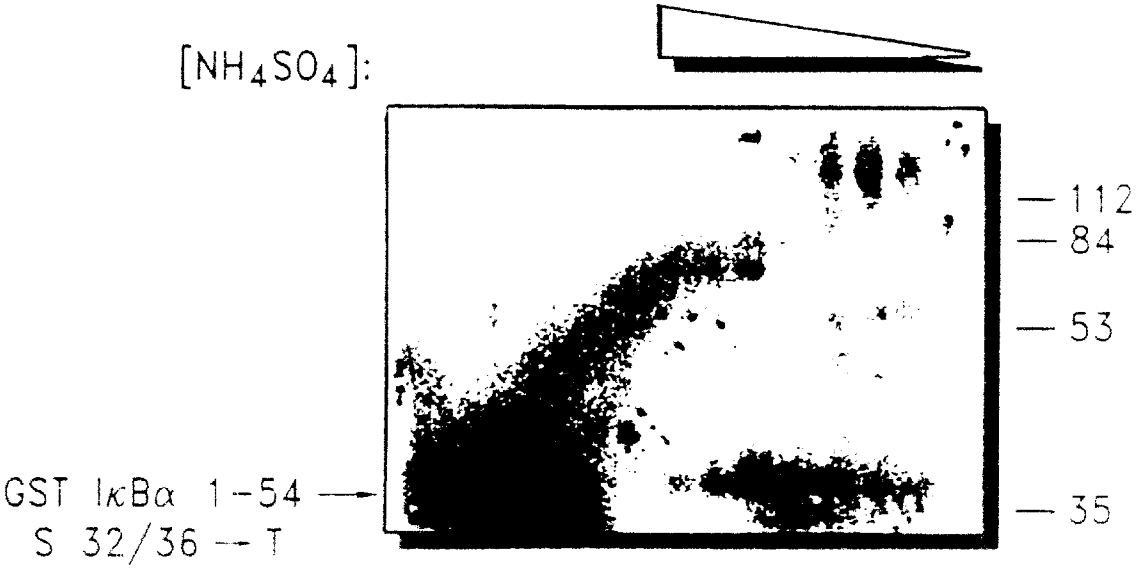

Following chromatographic fractionation by Q Sepharose, Superdex 200, MonoQ Sepharose and Phenyl Superose, in vitro kinase assay showed substantial purification of the IκB kinase activity (FIG. 6A). Further purification of the IκB kinase was achieved by passing the sample over, in series, an analytical Superdex 200 and Mono Q HR 5/5, resulting in 8 major protein bands as determined by silver staining. As before, the use of substrate containing threonine substitutions at positions 32 and 36 markedly reduced the phosphorylation (FIG. 6B). These results demonstrate the purification of a stimulus-inducible IκBα kinase complex, which specifically phosphorylates serine residues at positions 32 and 36 of IκBα without the addition of exogenous factors.

Example 4

Immunoprecipitation of IKK Signalsome Using Anti MKP-1 Antibodies

This Example illustrates the immunoprecipitation of IκB kinase activity from cytoplasmic extracts prepared from stimulated cells.

A. Immunoprecipitation of IκB Kinase Complex from HeLa Cells

HeLa cells were TNF-α-treated (30 μg/mL, 7 minutes) and fractionated by gel filtration as described in Example 3. Twenty μL of gel filtration fraction #6 (corresponding to about 700 kD molecular weight) and 1 μg purified antibodies raised against MKP-1 (Santa Cruz Biotechnology, Inc., Santa Cruz, Calif.) were added to 400 μL of ice cold 1×Pull Down Buffer (20 mM Tris pH 8.0, 250 mM NaCl, 0.05% NP-40, 3 mM EGTA, 5 mM EDTA, 10 mM β-glycerophosphate, 10 mM NaF, 10 mM PNPP, 300 μM $Na_3VO_4$, 1 mM benzamidine, 2 μM PMSF, 10 μg/ml aprotonin, 1 μg/ml leupeptin, 1 μg/ml pepstatin, 1 mM DTT). The sample was gently rotated for 1 hour at 4° C., at which time 40 μL of protein A-agarose beads (50:50 slurry, Santa Cruz Biotechnology, Inc., Santa Cruz, Calif.) was added. The sample was then rotated for an additional 1.5 hours at 4° C. The protein A-agarose beads were pelleted at 3,000 rpm for 2 minutes at 4° C. and the pellet was washed three times with ice cold Pull Down Buffer (800 μL per wash).

The pellet was subjected to the standard in vitro IκBα kinase assay (as described above) using either 2 μg GST-IκBα1–54 (wildtype) or 2 μg GST-IκBα1–54 (S32/36 to T) as the substrate.

Figure 7:
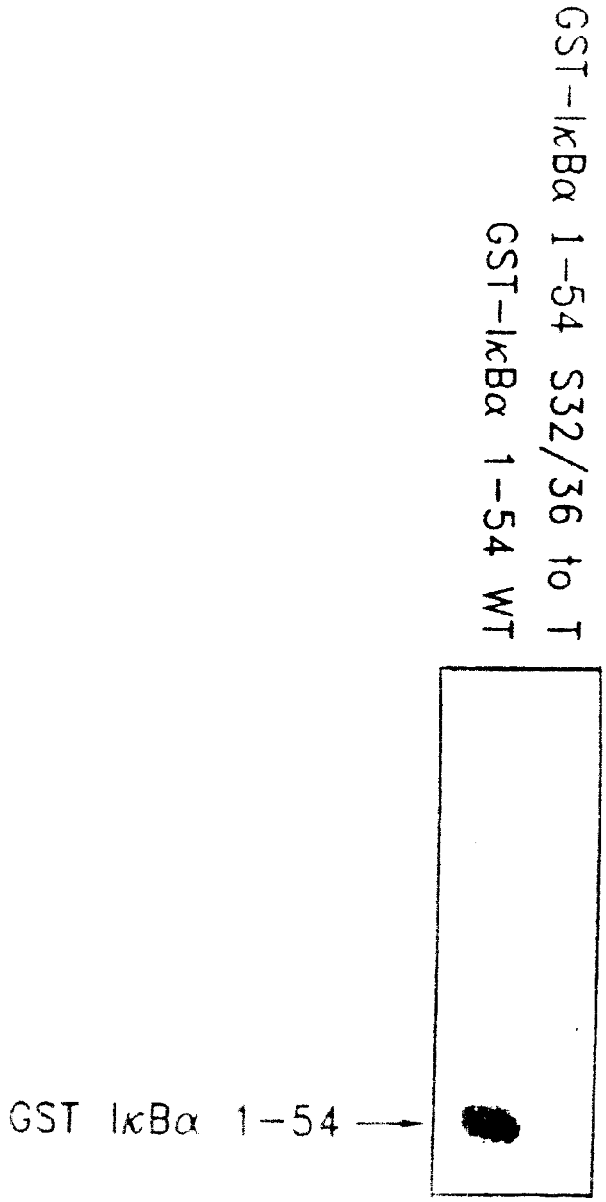
FIG. 7 is an autoradiogram showing the results of immunokinase assays (using anti-MKP-1 antibody) performed using cytoplasmic extracts of TNFα-treated HeLa S3 cells following gel filtration. The assay was performed using the substrates GST-IκBα1–54 wildtype (lane 1) and GST-IκBα1–54 S32/36 to T (lane 2). The positions of IκBα and GST-IκBα 1–54 are indicated on the left.

The results, shown in FIG. 7, demonstrate that antibodies directed against MKP-1 immunoprecipitate the stimulus-inducible IκBα kinase activity. The substrate specificity of this IκBα kinase activity corresponds to what has been described in vivo (strong phosphorylation of the GST-IκBα1–54 (wildtype) and no phosphorylation using GST-IκBα1–54 (S32/36 to T).

B. Characterization of Immunoprecipitated IKK Signalsome

For these studies, small scale immunoprecipitation were performed using two 150 mm plates of HeLa cells (one stimulated and one unstimulated). Whole cell lysates were diluted 4-fold with 2×Pull-Down Buffer (40 mM Tris pH 8.0, 500 mM NaCl, 0.1% NP-40, 6 mM EDTA, 6 mM EGTA, 10 mM β-glycerophosphate, 10 mM NaF, 10 mM PNPP, 300 μM $Na_3VO_4$, 1 mM benzamidine, 2 μM PMSF, 10 μg/ml aprotonin, 1 μg/ml leupeptin, 1 μg/ml pepstatin, 1 mM DTT) and 2-4 μg of the indicated antibody was added. Lysates were incubated on ice for 1–2 hours, 10 μl of Protein A or G beads were added, and lysates were left to incubate with gentle rotation for an additional 1 hour at 4° C. The immunoprecipitate was then washed 3 times with 2×Pull-Down Buffer, 1× with kinase buffer without ATP and subjected to a kinase assay as described in Example 2. There was no noticeable loss in IκB kinase activity when the immunoprecipitate was subjected to more rigorous washing, such as in RIPA buffer (20 mM Tris, 250 mM NaCl, 1% NP-40, 1% DOC, 0.1% SDS, 3 mM EDTA, 3 mM EGTA, 10 mM β-glycerophosphate, 10 mM NaF, 10 mM PNPP, 300 μM $Na_3VO_4$, 1 mM benzamidine, 2 μM PMSF, 10 μg/ml aprotonin, 1 μg/ml leupeptin, 1 μg/ml pepstatin, 1 mM DTT) or washes up to 3.5 M urea.

Figure 8A:
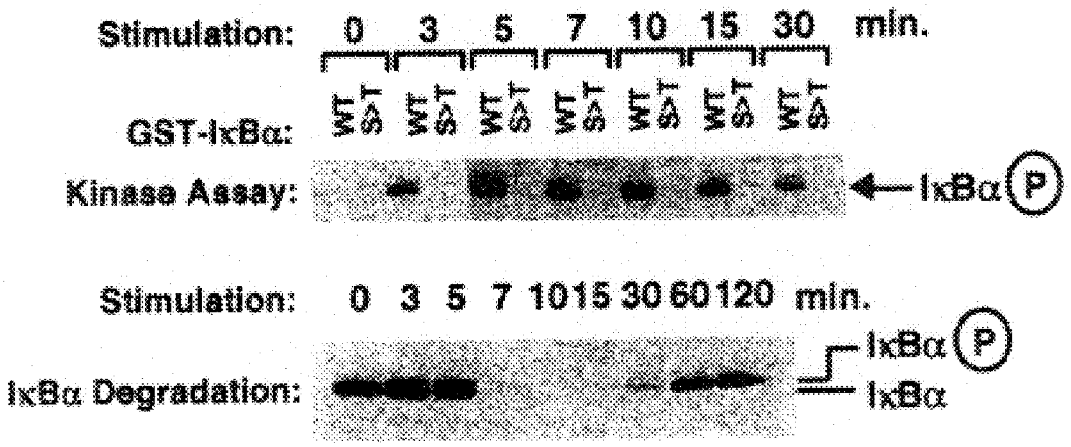
FIGS. 8A–8C are autoradiograms depicting the results of immunoblot analyses.
Figure 8B:
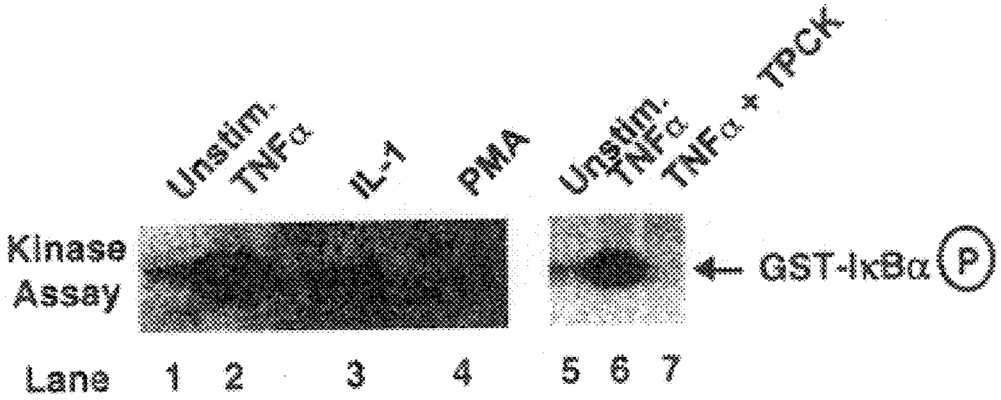
Figure 8C:
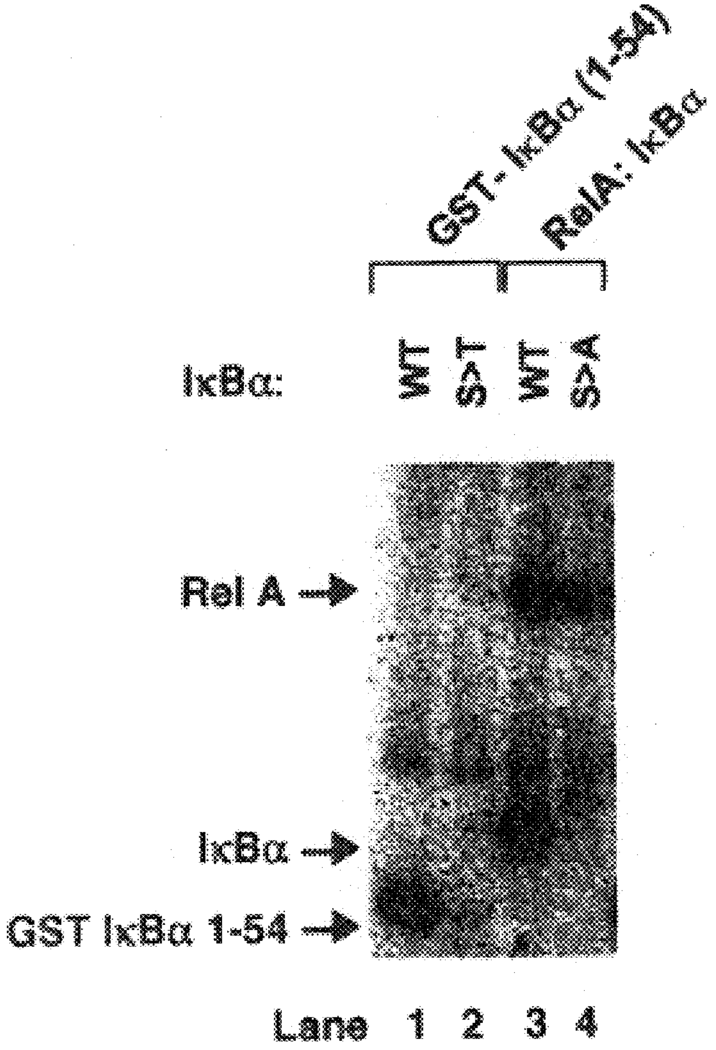

Of a large panel of antibodies tested, one of three anti-MKP-1 antibodies efficiently co-immunoprecipitated an inducible IκB kinase activity from HeLa cells as well as primary human umbilical vein endothelial cells (HUVEC). The co-immunoprecipitated kinase (IKK signalsome kinase) was inactive in unstimulated HeLa cells, but was rapidly activated within minutes of TNFα stimulation (FIG. 8A, top panel). The IKK signalsome kinase did not phosphorylate a mutant GST-IκBα protein in which serine residues 32 and 36 had been mutated to threonine (FIG. 8A top panel, even-numbered lanes). Activation of the signalsome kinase was maximal at 5 minutes and declined thereafter, a time course consistent with the time course of IκBα phosphorylation and degradation under the same conditions (FIG. 8A, bottom panel). As expected, the signalsome IκB kinase was also activated by stimulation of cells with IL-1 or PMA (FIG. 8B, lanes 1–4); moreover, its activity was inhibited in cells treated with TPCK, a known inhibitor of NFκB activation (FIG. 8B, lane 7). Additionally, the IKK signalsome kinase specifically phosphorylated full-length wild-type IκBα, but not a mutant IκBα bearing the serine 32, 36 to alanine mutations, in the context of a physiological RelA-IκBα complex (FIG. 8C, lanes 3, 4). Together these results indicate that the anti-MKP-1 antibody co-immunoprecipitated the IKK signalsome. The signalsome-associated IκB kinase met all the criteria expected of the authentic IκB kinase and had no detectable IκBα C-terminal kinase activity.

Figure 9A:
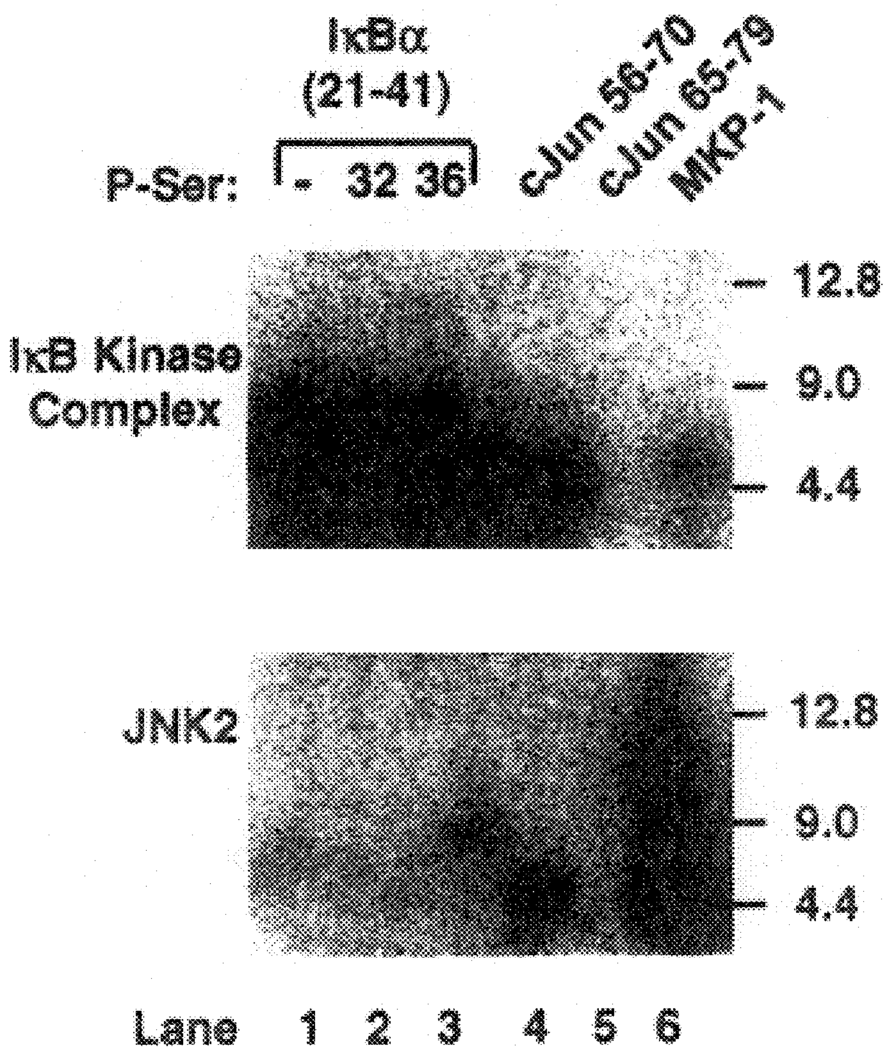
FIG. 9A is an autoradiogram depicting the results of an immunokinase assay in which peptides are phosphorylated by the IKK signalsome. In the top panel, IκBα(21–41) peptides that were unphosphorylated or chemically phosphorylated on either Ser-32 or Ser-36 were incubated with the IKK signalsome in the presence of γ-[$^{32}$P]-ATP. The doubly phosphorylated peptide P32,36 was not phosphorylated by the IKK signalsome, and the unrelated c-Fos (222–241) phosphopeptide with free serine and threonine residues did not function as a signalsome substrate.

The specificity of the IKK signalsome kinase was further established by kinetic analysis and by examining its activity on various peptides and recombinant protein substrates (FIG. 9A). For these studies, synthetic peptides (Alpha Diagnostics International, San Antonio, Tex.) were prepared with the following sequences:

IκBα(21–41): CKKERLLDDRHDSGLDSMKDEE (SEQ ID NO: 11)

IκBα(21–41) S/T mutant: CKKERLLDDRHDTGLDTMKDEE (SEQ ID NO: 12)

c-Fos(222–241): DLTGGPEVAT(PO3)PESEEAFLP (SEQ ID NO: 13)

MKP-1: CPTNSALNYLKSPITTSPS (SEQ ID NO: 14)

cJun(56–70): CNSDLLTSPDVGLLK (SEQ ID NO: 15)

cJun(65–79): CVGLLKLASPELERL (SEQ ID NO: 16)

Phosphorylation of these peptides (100 μM) was performed using a kinase reaction as described above. Reactions were for one hour at room temperature and were terminated by the addition of SDS-PAGE loading buffer. SDS-PAGE with a 16% Tris/tricine gel (Novex, San Diego, Calif.) or a 4–20% Tris/glycine gel (Novex, San Diego, Calif.) was used to characterize the reaction products. Gels were washed, dried in vacuo, and exposed to autoradiographic film.

Inhibition of immunopurified IKK signalsome activity was measured by $^{32}P$ incorporation into GST-IκBα(1–54) in a discontinuous assay using the reaction conditions described above. The concentrations of GST-IκBα(1–54) and ATP used in the inhibition studies were 0.56 μM and 3 μM, respectively. Enzymatic reactions (32 μL) were carried out in wells of a 96 well assay plate for one hour at room temperature and terminated with the addition of trichloroacetic acid (TCA) (150 μL/well of 12.5% w/v). The subsequent 20 minute incubation with TCA precipitated the proteins but not peptides from solution. The TCA precipitate was collected on 96-well glass fiber plates (Packard) and washed 10 times with approximately 0.3 mL per well of Dulbecco's phosphate buffered saline pH 7.4 (Sigma) using a Packard Filtermate 196. Scintillation fluid (0.50 mL, MicroScint, Packard) was added to each well and the plate was analyzed for $^{32}P$ using a Packard TopCount scintillation counter. Less than 10% of ATP was turned over in the course of the assay reaction, ensuring that the kinetic data represented initial rate data. The inhibition constant of the P32, 36 peptide was determined by Dixon analysis (Dixon and Webb, *In Enzymes* (Academic Press: New York, ed. 3, 1979), pp. 350–51.

Figure 9B:
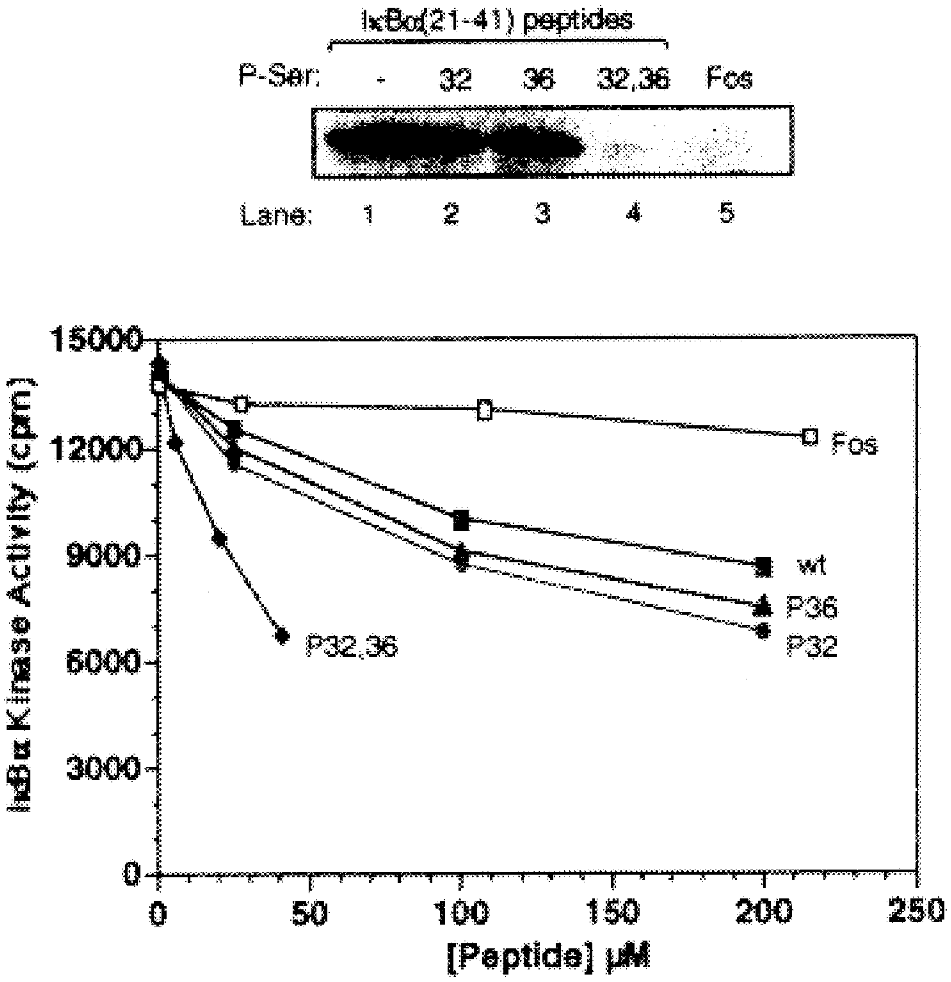
FIG. 9B is a graph illustrating the inhibition of phosphorylation of GST-IκBα (1–54) by IκBα(21–41) peptides. IκBα(21–41) peptide P32,36 inhibits GST-IκBα (1–54) as a product inhibitor with a $K_i$ value of 14 μM. The unrelated phosphopeptide c-Fos(222–241) does not function as an inhibitor. This assay only detects precipitated $^{32}$P-labeled proteins, not $^{32}$P-labeled peptides. Addition of the singly- or non-phosphorylated IκBα(21–41) peptides results in less phosphorylation of GST-IκBα (1–54) and apparent inhibition.

The kinase displayed normal Michaelis-Menten kinetics, suggesting that it was not a mixture of diverse unrelated kinases. The kinase was capable of phosphorylating an IκBα (21–41) peptide (FIGS. 9A and 9B)) as well as two different IκBα (21–41) peptides, each bearing a free serine at either position 32 or 36 and phosphoserine at the other position (FIGS. 9A and 9B, lanes 2, 3). As expected, a peptide with phosphoserines at both positions was not phosphorylated at all (FIG. 9B, top), indicating that there was no significant turnover of the phosphates under our reaction conditions. These experiments indicated that both serines 32 and 36 were phosphoacceptor sites for the IKK signalsome kinase, thus distinguishing it from other kinases such as pp90Rsk which phosphorylates IκBα only at serine 32 (Schouten, et al., *EMBO J.* 16:3133–44, 1997).

Although the IKK signalsome kinase efficiently phosphorylated IκB peptides, it did not phosphorylate the c-Fos phosphopeptide containing a free serine and a free threonine (FIG. 9B, top), two c-Jun peptides containing serine 63 and 73, respectively, (FIG. 9A, top panel, lanes 4, 5), or an MKP-1 peptide containing four serines and three threonines (FIG. 9A, lane 6). The latter peptides were substrates for JNK2 (FIG. 9A, bottom panel, lanes 4–6). An IκBα (21–41) peptide in which serines 32 and 36 were replaced by threonines was phosphorylated by the signalsome at least 10-fold less well than the wild-type serine-containing peptide, consistent with the slower phosphorylation and degradation kinetics of IκBα(S32/36 to T) in cells (DiDonato et al., *Mol. Cell. Biol.* 16:1295–1304, 1996), and the preference of the kinase for serine over threonine at positions 32, 36 in both full-length IκBα and GST-IκBα (1–54) (FIGS. 8A and C). In addition, the kinase phosphorylated GST-IκBβ (1–54), albeit with lower affinity. In most experiments, IκB kinase activity was also associated with strong RelA kinase activity (FIG. 8C, lanes 3, 4), but no activity was observed towards several other substrates including myelin basic protein (MBP), GST-ATF2 (1–112), GST-cJun (1–79), GST-ERK3, GST-Elk (307–428), GST-p38, and a GST fusion protein containing the C-terminal region of IκBα (242–314).

The specificity of the IKK signalsome kinase was further emphasized by its susceptibility to product inhibition (FIG. 9B, bottom). The kinase was strongly inhibited by a doubly-phosphorylated IκBα peptide bearing phosphoserines at both positions 32 and 36, but not by the unrelated c-Fos phosphopeptide that contained a single phosphothreonine. The singly-phosphorylated and the unphosphorylated IκBα peptides were less effective inhibitors.

Example 5

Absence of Free Ubiguitin in Purified IKK Signalsome

Figure 10:
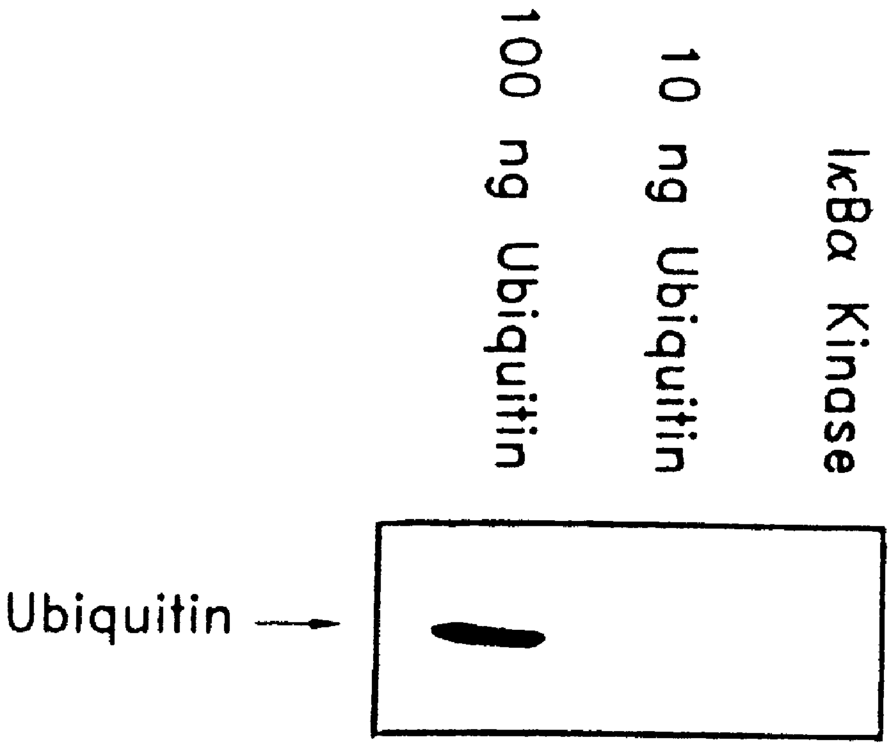
FIG. 10 is an autoradiogram showing the results of a western blot analysis of the level of ubiquitin within a stimulus-inducible IkB kinase complex. Lane 1 shows the detection of 100 ng ubiquitin, Lane 2 shows 10 ng ubiquitin and Lane 3 shows 3.4 μg of IKK signalsome purified through the phenyl superose step (sufficient quantities for 10 kinase reactions). The position of ubiquitin is shown by the arrow on the left.

This example illustrates the absence of detectable free ubiquitin with a IKK signalsome prepared as in Example 3. Standard western blot procedures were performed (Amersham Life Science protocol, Arlington Heights, Ill.). 100 ng ubiquitin, 10 ng ubiquitin and 20 μl purified IkBα kinase complex was subjected to 16% Tricine SDS-PAGE (Novex, San Diego, Calif.), transferred to Hybond ECL Nitrocellulose membrane (Amersham Life Science, Arlington Heights, Ill.), and probed with antibodies directed against ubiquitin (MAB1510; Chemicon, Temecula, Calif.). The results are shown in FIG. 10. Free ubiquitin could not be detected in the purified IkBα kinase preparation (even at very long exposures). The complexes described herein do not require addition of endogenous ubiquitin to detect IkBα kinase activity, nor is free ubiquitin a component in the purified IkBα kinase preparations of the present invention.

Example 6

Purification of the NFκB Signalsome and Identification of IKK-1 and IKK-2

This Example illustrates a two-step affinity method for purification of the IKK signalsome, based on its recognition by the MKP-1 antibody (depicted in FIG. 11A) and the identification of IκB kinases.

For large scale IKK signalsome purification, HeLa S3 cells were stimulated for 7 minutes with 20 ng/ml TNFα (R&D Systems, Minneapolis, Minn.), harvested, whole cell lysates were prepared (1.2 g total protein) and approximately 5 mg of anti-MKP-1 antibody (Santa Cruz Biotechnology, Inc., Santa Cruz, Calif.) was added and incubated at 4° C. for 2 hours with gentle rotation. Subsequently, 50 ml of Protein A agarose (Calbiochem, San Diego, Calif.) was added and the mixture was incubated for an additional 2 hours. The immunoprecipitate was then sequentially washed 4×Pull-Down Buffer, 2×RIPA buffer, 2×Pull-Down Buffer, 1×3.5 M urea-Pull-Down Buffer and 3×Pull-Down Buffer. The immunoprecipitate was then made into a thick slurry by the addition of 10 ml of Pull-Down Buffer, 25 mg of the specific MKP-1 peptide to which the antibody was generated (Santa Cruz Biotechnology, Inc., Santa Cruz, Calif.) was added, and the mixture was incubated overnight at 4° C. with gentle rotation. The eluted IKK signalsome was then desalted on PD 10 desalting columns (Pharmacia Biotech, Piscataway, N.J.) equilibrated with 50 mM Q buffer and chromatographed on a Mono Q column (Pharmacia Biotech, Piscataway, N.J.). Fractions containing peak IkB kinase activity were pooled, concentrated and subjected to preparative SDS-PAGE. The intensity of two prominent protein bands of ~85 and ~87 kDa (indicated by silver stain in FIG. 11B as IKK-1 and IKK-2 respectively) correlated with the profile of IκB kinase activity.

Coomassie stained ~85 and ~87 kDa bands were excised, in-gel digested with trypsin (Wilm et al., *Nature* 37:466–69, 1996) and a small aliquot of the supernatant was analyzed by high mass accuracy MALDI peptide mass mapping, as described by Shevchenko et al., *Proc. Natl. Acad. Sci. USA* 93:14440–45, 1996. The peptide mass map from the IKK-1 band was searched against a comprehensive protein sequence database using the program PeptideSearch developed in house at EMBL Heidelberg. Eight measured peptide masses matched calculated tryptic peptide masses from CHUK (conserved helix-loop-helix ubiquitous kinase; Connely and Marcu, *Cell. Mol. Biol. Res.* 41:537–49, 1995) within 30 ppm, unambiguously identifying the protein. The peptide mass map of the IKK-2 band did not result in a clear identification and therefore the sample was subjected to nanoelectrospray mass spectrometry (Wilm and Mann, *Anal. Chem.* 68:1–8, 1996). The peptide mixture obtained after extraction of the gel piece was micropurified on a capillary containing 50 nL of POROS R2 resin (PerSeptive Biosystems, Framingham, Mass.). After washing, the peptides were step-eluted with 0.5 μl of 50% MeOH in 5% formic acid into a nanoelectrospray needle. This needle was transferred to an APIII mass spectrometer (Perkin-Elmer, Sciex, Toronto, Canada) and the sample sprayed for approximately 20 minutes. During this time, peptide ions apparent from the mass spectrum were selected and isolated in turn and fragmented in the collision chamber of the mass spectrometer. From the tandem mass spectra, short stretches of sequence were assembled into peptide sequence tags (Mann and Wilm, *Anal. Chem.* 66:4390–99, 1994) and searched against a protein sequence database or against dbEST using PeptideSearch.

Three peptides matched the IKK-1 sequence. A1: IIDLGYAK (SEQ ID NO:17); A2: VEVALSNIK (SEQ ID NO:18); A3 SIQLDLER (SEQ ID NO:19). Three other peptides matched human EST sequences in dbEST: B1: ALELLPK (SEQ ID NO:20), B2: VIYTQLSK (SEQ ID NO:21), B6: LLLQAIQSFEK (SEQ ID NO:22) all match EST clone AA326115. The peptide B4 with the sequence LGTGGFGNVIR (SEQ ID NO:23) was found in clone R06591. After the full-length IKK-2 sequence was obtained (as described below) two more peptides B3: ALDDILNLK (SEQ ID NO:24) and B5: DLKPENIVLQQGEQR (SEQ ID NO:25) were found in the sequence. Peptide A1 is present in both IKK-1 and IKK-2 sequences. All the EST clones identified were clearly homologous to human and mouse CHUK, a serine/threonine kinase of hitherto unknown function. Once the complete coding sequence of IKK-2 was obtained (as described below), all sequenced peptides (apart from two peptides derived from IKK-1) could be assigned to this protein.

Figure 12A:
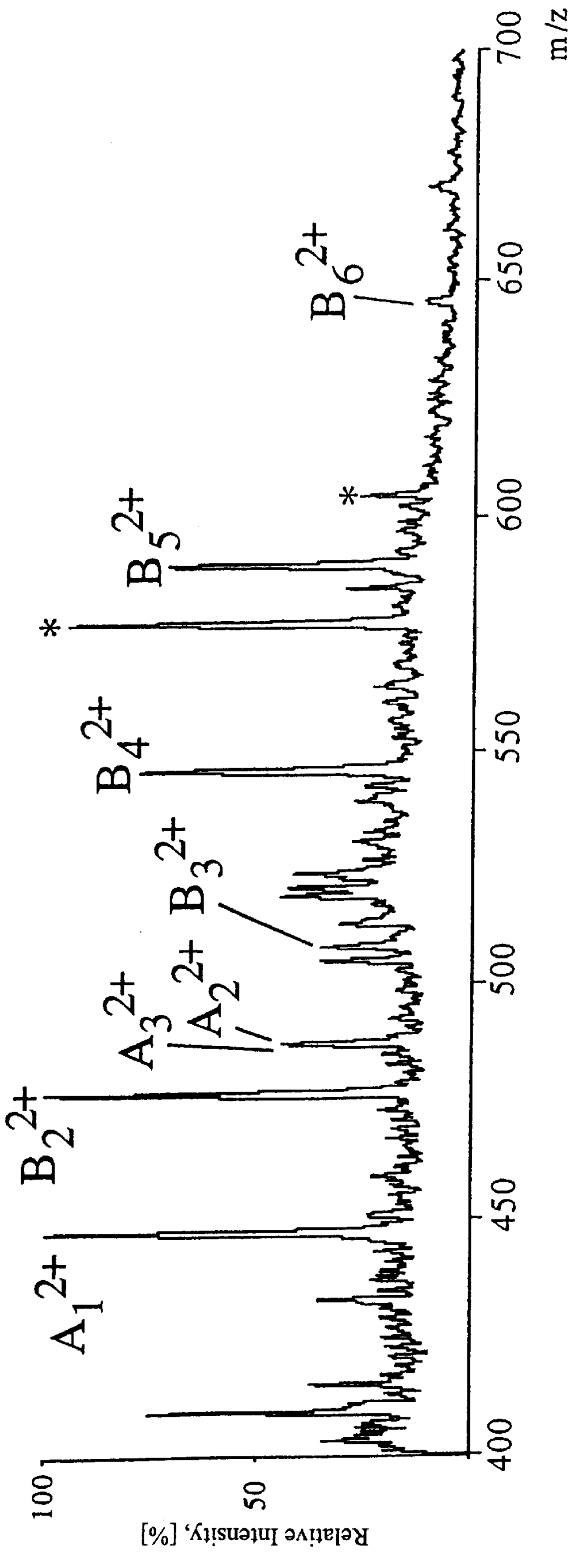
FIGS. 12A and 12B are mass spectra obtained during sequencing of IKK-2 by nanoelectrospray mass spectrometry.
Figure 12B:
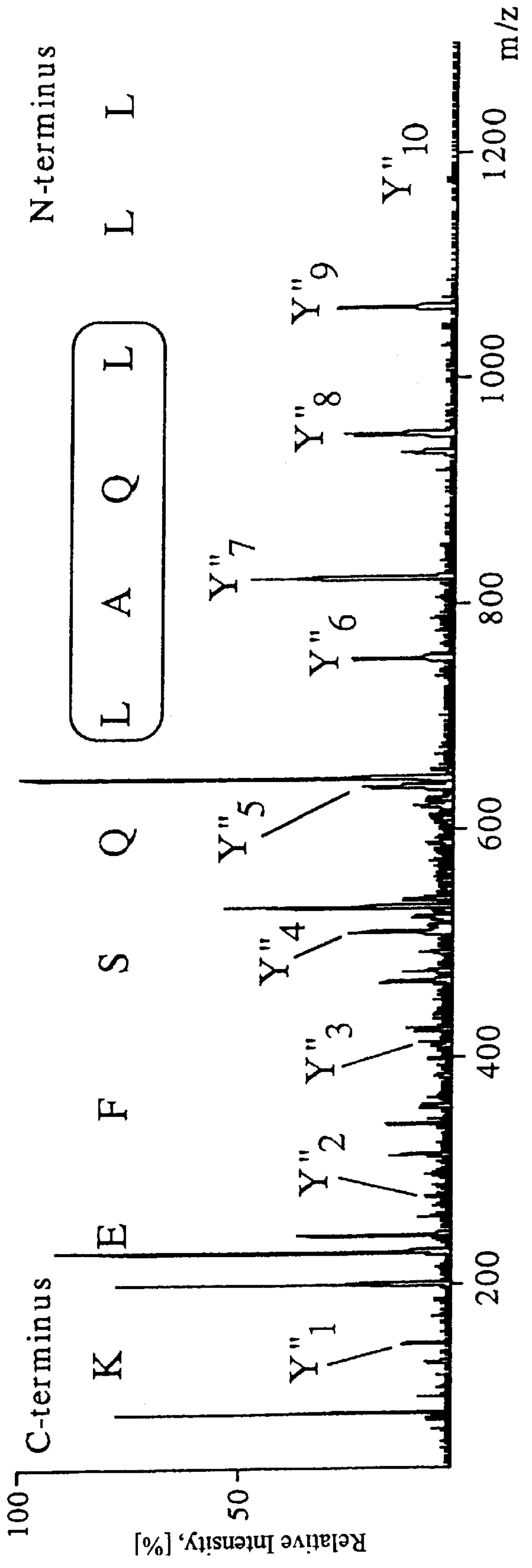

Representative mass spectra are shown in FIGS. 12A and 12B. In FIG. 12A, peaks labeled A were matched to the tryptic peptides of IKK-1 upon fragmentation followed by database searching with peptide sequence tags. Peaks labeled B2, B4, B6 were not found in protein databases but instead matched human EST sequences. One more peptide (B1) matching a human EST clone was observed at m/z 392.2 and is not shown in panel A. In FIG. 12B, a continuous series of C-terminal-containing fragments (Y"-ions) was used to construct a peptide sequence tag as shown by boxed letters. Search of this tag resulted in a match to the peptide LLLQALQSFEK (SEQ ID NO:22) in human EST clone AA326115. Two more peptides, B1 (ALELLPK; SEQ ID NO:20) and B2 (VIYTQLSK; SEQ ID NO:21) were found in the sequence of the same EST clone.

Full-length human IKK-1 and IKK-2 cDNAs were cloned based on the. human EST clones, which were obtained from Genome Systems, Inc. (St. Louis, Mo.). The precise nucleotide sequences were determined and used to design primers to PCR clone human IKK-2 from a human HeLa cell cDNA library (Clontech, Inc., Palo Alto, Calif.). Several IKK-2 cDNA clones were isolated and sequenced. Full-length mouse IKK-1 and a partial human IKK-1 nucleotide sequence was available in the comprehensive database, primers were designed to PCR clone the respective human and mouse IKK-1 cDNAs. The partial human IKK-1 coding region was used to probe a HeLa cDNA phage library (Stratagene, Inc., La Jolla, Calif.) to obtain the full-length human IKK-1 cDNA clone using standard procedures.

Sequence analysis of these clones revealed that IKK-1 and IKK-2 were related protein serine kinases (51% identity) containing protein interaction motifs (FIG. 13A). Both IKK-1 and IKK-2 contain the kinase domain at the N-terminus, and a leucine zipper motif and a helix-loop-helix motif in their C-terminal regions (FIG. 13A). Northern analysis indicated that mRNAs encoding IKK-2 were widely distributed in human tissues, with transcript sizes of ~4.5 kb and 6 kb (FIG. 13B). The distribution of IKK-1 (CHUK) transcripts has been reported previously (Connely et al., *Cell. Mol. Biol. Res.* 41:537–49, 1995). IKK-1 and IKK-2 mRNAs are constitutively expressed in Jurkat, HeLa and HUVEC cell lines, and their levels are not altered for up to 8 hours following stimulation with NFκB inducers such as TNFα (HeLa, HUVEC) or anti-CD28 plus PMA (Jurkat).

To further characterize the properties of IKK-1 and IKK-2, recombinant HA-tagged IKK-1 and Flag-tagged IKK-2, either separately or alone, were in vitro transcribed and translated in wheat germ or rabbit reticulocyte lysate (Promega, Madison, Wis.). The reactions were performed exactly as described in the manufacturer's protocol. Epitope-tagged IKK-1 and IKK-2 then immunoprecipitated with the appropriate anti-tag antibody. Immunoprecipitates containing these proteins phosphorylated IκBα and IκBβ with the correct substrate specificity (i.e., immunoprecipitates of IKK-1 and IKK-2 phosphorylated both GST-IκBα (FIG. 14A, panel 3) and GST-IκBβ (panel 4), but did not phosphorylate the corresponding S32/36 to T mutant protein). IKK-1 expressed in rabbit reticulocyte lysates was also capable of autophosphorylation (FIG. 14A, panel 2, lane 1), whereas a kinase-inactive version of IKK-1, in which the conserved lysine 44 had been mutated to methionine, showed no autophosphorylation. In contrast IKK-2, although expressed at equivalent levels in the lysates (panel 1), showed very weak autophosphorylation (panel 2, lane 2).

Figure 14B:
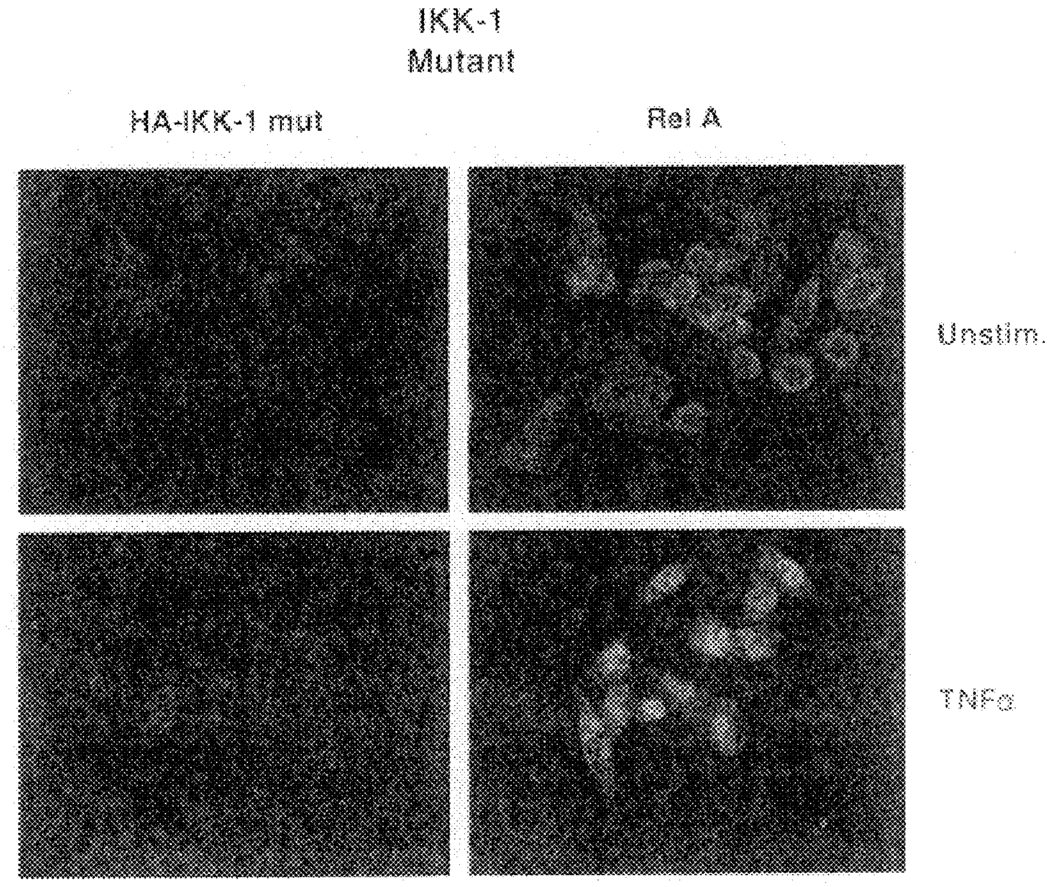
FIGS. 14B and 14C are micrographs illustrating the results of assays to evaluate the ability of kinase-inactive mutants of IKK-1 and IKK-2 to inhibit RelA translocation in TNFα-stimulated HeLa cells. HeLa cells were transiently transfected with either HA-tagged IKK-1 K44 to M mutant (14B) or Flag-tagged IKK-2 K44 to M mutant (14C) expression vectors. 36 hours post-transfection cells were either not stimulated (Unstim) or TNFα-stimulated (20 ng/ml) for 30 min (TNFα), as indicated to the right of the figure. Cells were then subjected to immunofluorescence staining using anti-HA of anti-Flag antibodies to visualize expression of IKK-1 K44 to M or IKK-2 K44 to M, respectively. Stimulus-dependent translocation of Rel A was monitored using anti-Rel A antibodies. Antibodies used are indicated to the top of the figure. IKK mutant transfected is indicated to the left of the figure.
Figure 14C:
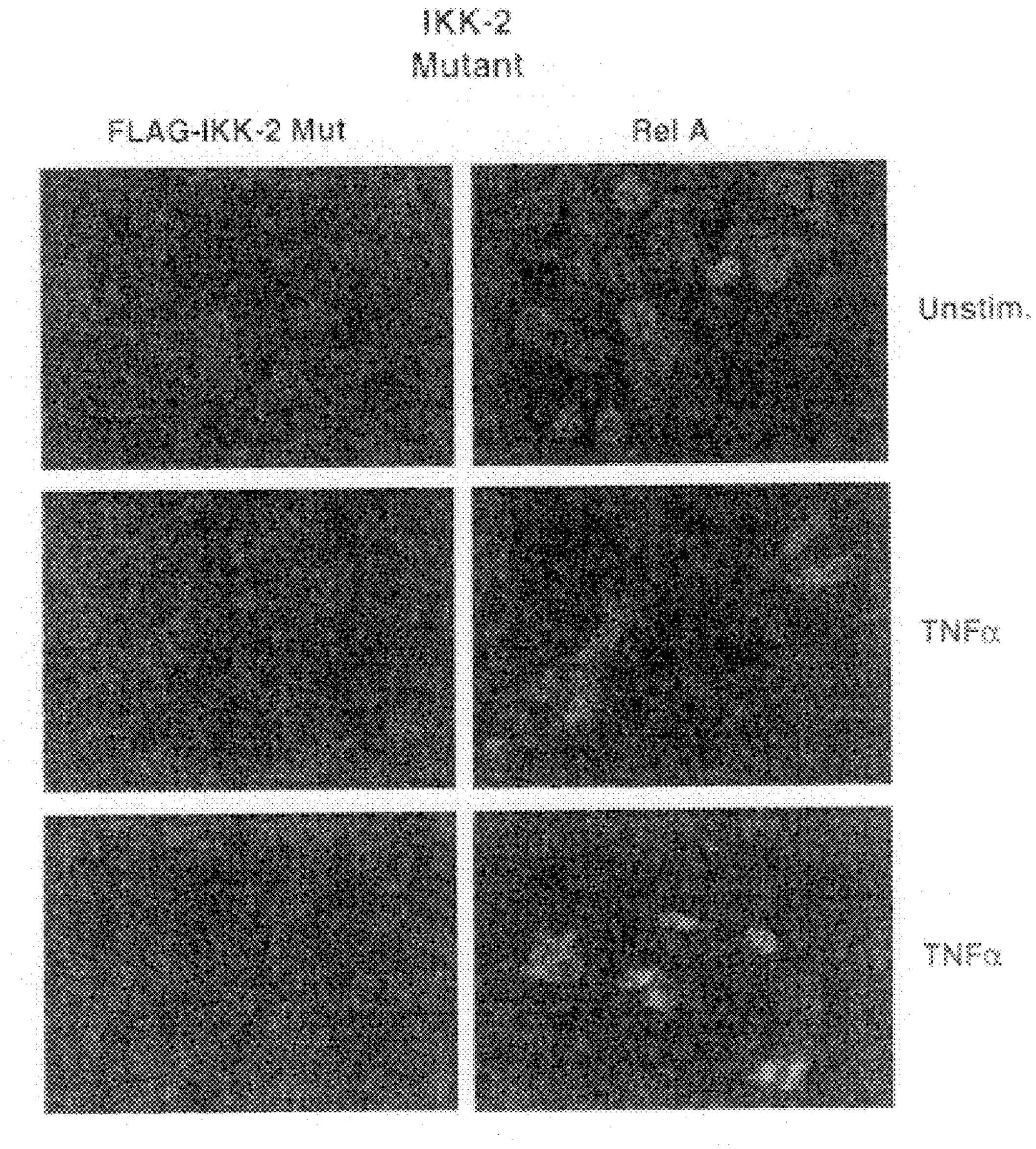

Expression of the kinase inactive mutants (K to M) of IKK-1 and IKK-2 indicate that both play critical roles in NFκB activation as demonstrated by immunofluorescent studies (FIGS. 14B and 14C). For these studies, HeLa cells were transiently transfected with either HA-tagged IKK-1 or Flag-tagged IKK-2. Cells were fixed for 30 minutes with methanol. For immunofluorescence staining, the cells were incubated sequentially with primary antibody in PBS containing 10% donkey serum and 0.25% Triton X-100 for 2 hours followed by fluorescein-conjugated or Texas red-conjugated secondary antibody (Jackson Immunoresearch Laboratories, Inc., West Grove, Pa.; used at 1:500 dilution) for 1 hour at room temperature. The coverslips were rinsed and coverslipped with Vectashield (Vector Laboratories, Burlingame, Calif.) before scoring and photographing representative fields. Primary antibodies used for immunofluorescence staining included antibodies against Rel A (Santa Cruz Biotechnology, Inc., Santa Cruz, Calif.), HA tag (Babco, Berkeley, Calif.) and Flag tag (IBI-Kodak, New Haven, Conn.).

Kinase-inactive versions (K44 to M) of IKK-1 and IKK-2 had no effect on the subcellular localization of RelA in unstimulated HeLa cells, since RelA remained cytoplasmic both in cells expressing the epitope-tagged proteins and in the adjacent untransfected cells (FIGS. 14B and 14C, top panels). In contrast, both mutant proteins inhibited RelA nuclear translocation in TNFα-stimulated cells (FIGS. 14B and 14C, bottom panels). The inhibition mediated by the IKK-2 mutant was striking and complete (FIG. 14C: compare mutant IKK-2-expressing cells with untransfected cells in the same field), whereas that mediated by the mutant IKK-1 protein, expressed at apparently equivalent levels, was significant but incomplete (FIG. 14B). This difference in the functional activities of the two mutant kinases may point to distinct roles for these two kinases in NFκB activation.

Figure 15A:
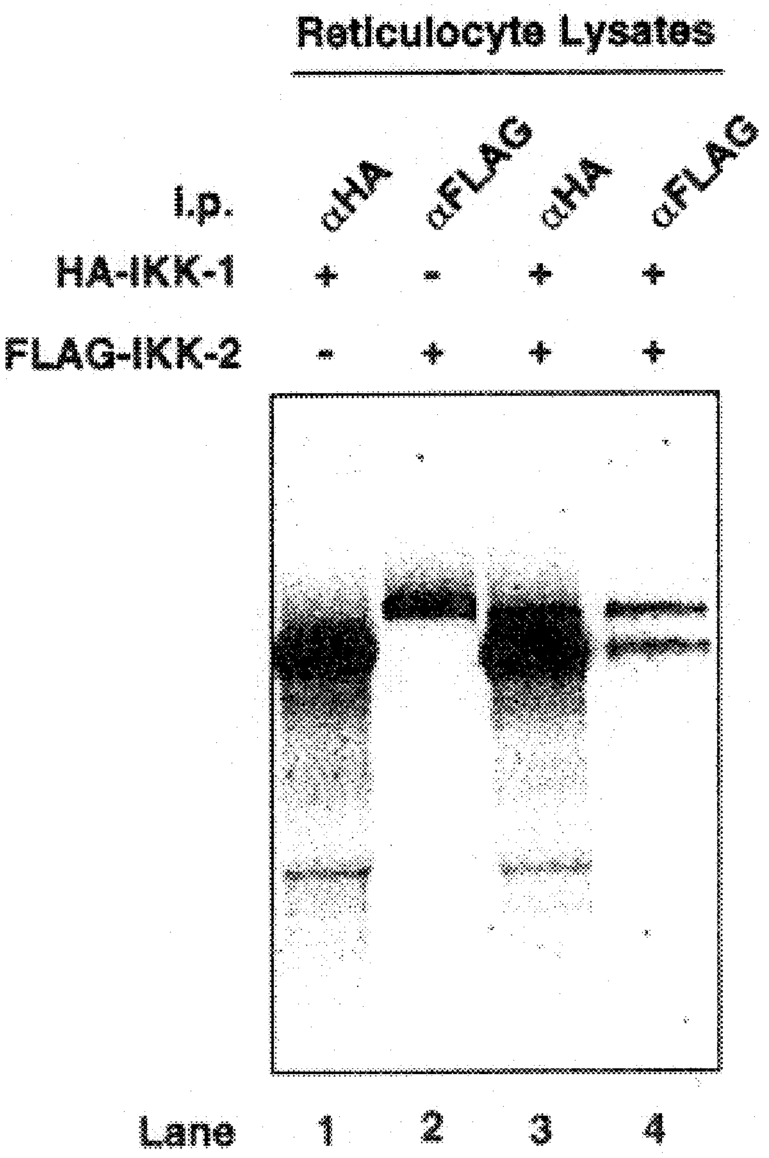
FIGS. 15A and 15B are autoradiograms of immunoprecipitated IKK-1 and IKK-2 following in vitro translation.
Figure 15B:
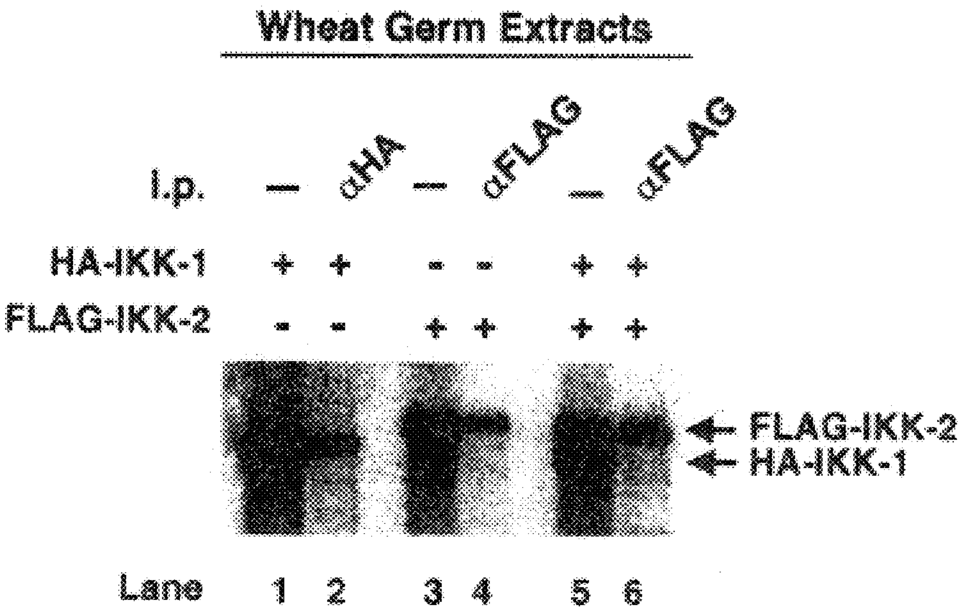

The presence of the leucine zipper and helix-loop-helix motif in IKK-1 and IKK-2 suggested that they interacted functionally with other proteins in the signalsome. An obvious possibility was that the proteins formed hetero- or homodimers with one another. HA-tagged IKK-1 and FLAG-tagged IKK-2 were translated in rabbit reticulocyte lysates, either alone or together, and then immunoprecipitated with antibodies to the appropriate epitope tags. This experiment demonstrated clearly that IKK-2 was present in IKK-1 immunoprecipitates (FIG. 15A, lane 3) and vice versa (lane 4), suggesting that these proteins either associated directly or via adapter proteins/IKK signalsome components present in the rabbit reticulocyte lysates. In contrast, however, there was no evidence for association of IKK-1 and IKK-2 that had been cotranslated in wheat germ lysates (FIG. 15B), suggesting that the proteins did not heterodimerize directly. When full-length IKK-1 was translated together in wheat germ extracts with a truncated version of IKK-1 that still possessed the protein interaction motifs, there was also no evidence of association, suggesting that IKK-1 was also not capable of forming homodimers under these conditions.

Both IKK-1 and IKK-2 kinases were active when expressed in wheat germ extracts, since they were capable of autophosphorylation, but they were inactive with respect to phosphorylation of IκB substrates. Since both autophosphorylation and substrate phosphorylation were intact in rabbit reticulocyte lysates, there appeared to be a direct correlation between the association of IKK-1 and IKK-2 into a higher order protein complex and the presence of specific IκB kinase activity in IKK-1 and IKK-2 immunoprecipitates. This higher order complex is most likely the IKK signalsome itself. Indeed, immunoprecipitation of rabbit reticulocyte lysates with anti-MKP-1 antibody pulls down a low level of active IκB kinase activity characteristic of the IKK signalsome.

Figure 11B:
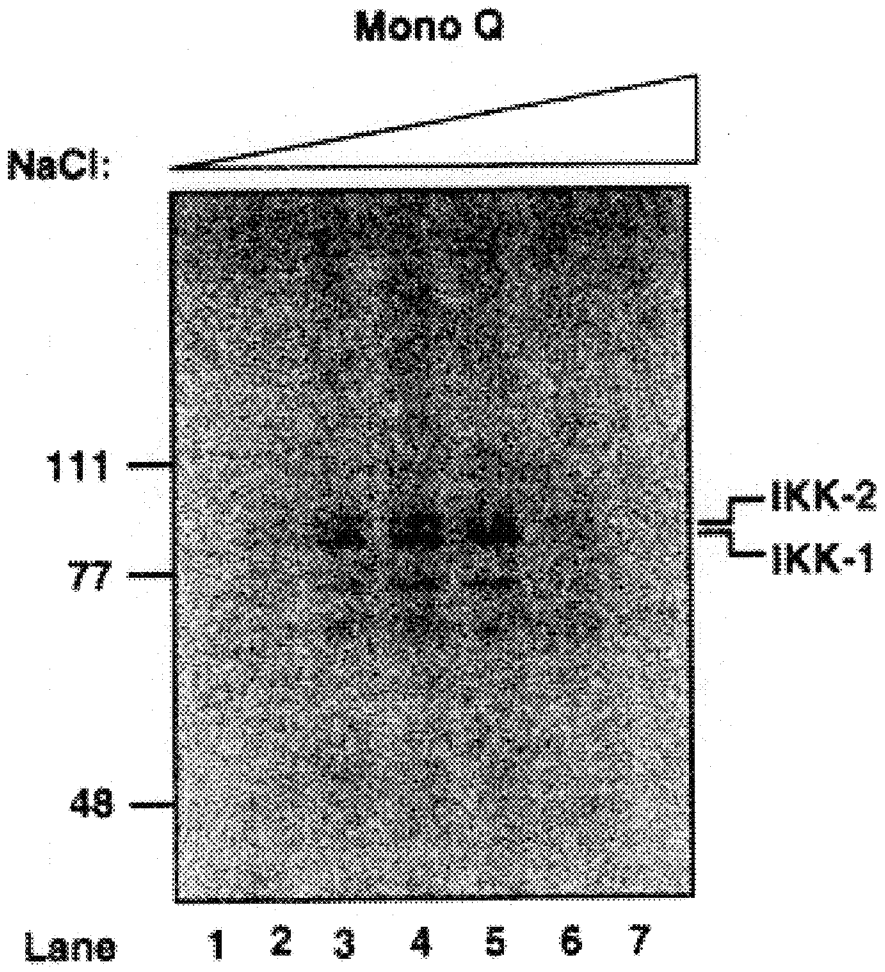
FIG. 11B is a photograph showing Mono Q fractions containing active IKK signalsome activity following SDS-PAGE and a standard silver stain protocol. Peak activity of IKK signalsome activity is represented in lanes 3, 4, and 5. Protein bands corresponding to IKK-1 and IKK-2 are indicated to the left of the figure. Molecular weight standards (kDa) are indicated to the left of the figure.

It is clear that the IKK signalsome contains multiple protein components in addition to IKK-1 and IKK-2 (FIG. 11B). Some of these may be upstream kinases such as MEKK-1 (Chen et al., *Cell* 84:853–62, 1996) or NIK (Malinin, et al., *Nature* 385:540–44, 1997); others may be adapter proteins that mediate the IKK-1:IKK-2 interaction. Indeed MEKK-1 copurifies with IKK signalsome activity (FIG. 1C), and two other signalsome proteins have been functionally identified. The protein crossreactive with anti-MKP-1 is an intrinsic component of the IKK signalsome kinases, since the IκB kinase activity coprecipitated with this antibody is stable to washes with 2-4 M urea Moreover, both IKK-1 immunoprecipitates and MKP-1 immunoprecipitates containing the IKK signalsome (FIG. 8C) contain an inducible RelA kinase whose kinetics of activation parallel those of the IκB kinase in the same immunoprecipitates. Another strong candidate for a protein in the signalsome complex is the E3 ubiquitin ligase that transfers multiubiquitin chains to phosphorylated IκB (Hershko et al., *Annu. Rev. Biochem.* 61:761–807,1992).

These results indicate that IKK-1 and IKK-2 are functional kinases within the IKK signalsome, which mediate IκB phosphorylation and NFκB activation. Appropriate regulation of IKK-1 and IKK-2 may require their assembly into a higher order protein complex, which may be a heterodimer facilitated by adapter proteins, the complete IKK signalsome, or some intermediate subcomplex that contains both IKK-1 and IKK-2.

From the foregoing, it will be appreciated that, although specific embodiments of the invention have been described herein for the purpose of illustration, various modifications may be made without deviating from the spirit and scope of the invention.

What is claimed is:

1. A method for phosphorylating a substrate of an IKK signalsome comprising contacting a with an isolated IKK signalsome capable of specifically phosphorylating IκBα at residues S32 and S36, and IkBβ at residues 19 and 23, without the addition of exogenous cofactors and thereby phosphorylating the substrate.

2. A method for phosphorylating a substrate of an IKK signalsome, comprising contacting a substrate with an isolated polypeptide comprising a component of an IKK signalsome having IkB kinase activity, and thereby phosphorylating the substrate.

3. A method according to claim 2, wherein the polypeptide comprises IKK-1 (SEQ ID NO:10).

4. A method according to claim 2, wherein the polypeptide comprises IKK-2 (SEQ ID NO:9).

5. The method of either of claim 1 or 2, wherein the substrate is IκBα or a variant thereof.

6. A method for screening for an agent that modulates IKK signalsome activity, comprising:

(a) contacting a candidate agent with an IKK signalsome capable of specifically phosphorylating IκBα at residues S32 and S36, and IκBβ at residues 19 and 23, without the addition of exogenous cofactors, wherein the step of contacting is carried out under conditions and for a time sufficient to allow the candidate agent and the IKK signalsome to interact; and (b) subsequently measuring the ability of the candidate agent to modulate an IKK signalsome activity.

7. A method according to claim 6, wherein the IKK signalsome activity modulated is selected from the group consisting of IκB kinase activity, p65 kinase activity and IKK phosphatase activity.

8. A method for screening for an agent that modulates IKK signalsome activity, comprising:

(a) contacting a candidate agent with a polypeptide comprising a component of an IKK signalsome capable of specifically phosphorylating IκBα at residues S32 and S36, and IκBβ at residues 19 and 23, without the addition of exogenous cofactors, wherein the step of contacting is carried out under conditions and for a time sufficient to allow the candidate agent and the polypeptide to interact; and (b) subsequently measuring the ability of the candidate agent to modulate the ability of the polypeptide to phosphorylate an IκB protein.

9. A method according to claim 8, wherein the polypeptide comprises IKK-1 (SEQ ID NO:10).

10. A method according to claim 8, wherein the polypeptide comprises IKK-2 (SEQ ID NO:9).

* * * * *

UNITED STATES PATENT AND TRADEMARK OFFICE

CERTIFICATE OF CORRECTION

PATENT NO. : 6,576,437 B2
DATED : December 31, 2003
INVENTOR(S) : Mercurio et al.

It is certified that error appears in the above-identified patent and that said Letters Patent is hereby corrected as shown below:

Column 57,
Line 18, insert -- substrate -- after "comprising contacting a".

Signed and Sealed this

Ninth Day of March, 2004

JON W. DUDAS
*Acting Director of the United States Patent and Trademark Office*